(12) United States Patent
Jones et al.

(10) Patent No.: US 6,395,800 B1
(45) Date of Patent: *May 28, 2002

(54) POLYMERIC BLENDS WITH ZWITTERIONIC GROUPS

(75) Inventors: Stephen Alister Jones; Peter William Stratford, both of Middlesex; Steven Rimmer, Lancs, all of (GB)

(73) Assignee: Biocompatibles Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/549,597

(22) Filed: Apr. 14, 2000

Related U.S. Application Data

(60) Continuation of application No. 09/013,033, filed on Jan. 26, 1998, now Pat. No. 6,150,432, which is a division of application No. 08/290,901, filed as application No. PCT/GB93/02652 on Dec. 23, 1993.

(30) Foreign Application Priority Data

Dec. 23, 1992 (GB) .......................... 92267913

(51) Int. Cl.$^7$ .................... C08L 101/00; C08L 101/02
(52) U.S. Cl. .................... 523/105; 523/106; 523/331; 523/340; 524/510; 524/515; 524/521; 524/523; 524/547; 525/183; 525/217
(58) Field of Search .................... 523/105, 106, 523/331, 340; 524/510, 515, 521, 523, 547; 525/183, 217

(56) References Cited

U.S. PATENT DOCUMENTS

| | | | | |
|---|---|---|---|---|
| 3,862,079 A | * | 1/1975 | Plueddemann | 524/512 |
| 4,140,664 A | | 2/1979 | Mizuguchi et al. | 524/539 |
| 4,585,835 A | | 4/1986 | Saegusa et al. | 525/430 |
| 4,619,965 A | * | 10/1986 | Ishii et al. | 524/547 |
| 5,089,252 A | | 2/1992 | Grollier et al. | 424/47 |
| 5,208,295 A | | 5/1993 | Chaudhun et al. | 525/382 |
| 5,648,442 A | | 7/1997 | Bowers et al. | 526/277 |
| 5,705,583 A | | 1/1998 | Bowers et al. | 526/277 |
| 5,712,326 A | | 1/1998 | Jones et al. | 523/105 |
| 6,150,432 A | * | 11/2000 | Jones et al. | 523/105 |

FOREIGN PATENT DOCUMENTS

| | | |
|---|---|---|
| EP | 0079197 | 5/1983 |
| EP | 0208421 | 1/1987 |
| GB | 2113245 | 8/1983 |
| GB | 2161823 | 1/1986 |
| JP | 5463025 | 5/1979 |
| JP | A5548261 | 6/1980 |
| JP | A 10 176021 | 6/1998 |

OTHER PUBLICATIONS

"Improvement of Blood compatibility on Cellulose Dialysis Membrane 2. Blood Compatibility . . . ", K. Ishihara et al., Biomaterials 1992, vol. 13, No. 4, pp. 235–239.

"Biointeractions' 90, Biomaterials for the Nineties", Aug. 21–23, 1990, St. Catherine's College, Oxford, UK, Biomaterials 1991, vol. 12, No. 2, Mar. 1991, Kojima et al.

"Anti–Thrombogenous Haemodialysis Membranes", Nobuo Nakabayashi, vol. 8, N. 6 Issued 1$^{st}$ Jan. 1991, published Aug. 1991, the Specialist Bio Magazine for Industrialization of the Bio–Industry.

* cited by examiner

*Primary Examiner*—Peter Szekely
(74) *Attorney, Agent, or Firm*—Sughrue Mion, PLLC

(57) ABSTRACT

The biocompatibility of various polymers are improved by blending with them a polymer including a zwitterionic group. The zwitterionic group is usually an ammonium phosphate ester zwitterionic group and the polymer containing it may be produced by the free radical polymerisation of ethylenically unsaturated monomers including a monomer bearing the zwitterionic group. Blending of the two polymers may be achieved by dry blending particulate polymers or by mixing the polymers in liquid dispersion or solution followed by removal of the liquid medium. The fibrinogen absorption and/or platelet activation of polymers may be reduced to a value of less than 80% or even less than 60% of the base polymer by introducing amounts of more than 10% or more than 30% of the zwitterionic group containing polymer. Preferred blends are of copolymers of 2-(methacryloyloxyethyl)-2'-(trimethylammonium)ethyl phosphate inner salt with higher alkyl(meth)acrylate, blended with olefin polymers and/or with rubber latices. The products may be used in medical devices in which they come into contact with bodily fluids, especially blood, plasma, serum and/or tear film.

29 Claims, No Drawings

POLYMERIC BLENDS WITH ZWITTERIONIC GROUPS

This is a continuation of application Ser. No. 091013,033 filed Jan. 26, 1998, now U.S. Pat. No. 6,150,432 the disclosure of which is incorporated herein by reference, which is a divisional of application Ser. No. 08/1290,901 filed Dec. 5, 1994 and issued as U.S. Pat. No. 5,712,326 which is a 371 of PCT/GB93/02652 filed Dec. 23, 1993.

The present invention relates to new polymeric materials, especially suitable for use in biomedical applications, processes for their production, articles formed from such materials and processes for modifying the physical and biological properties of plastic materials. The medical device industry frequently employs a range of thermoplastic, elastomeric and thermoset materials in medical devices. Many of these polymers were originally developed as engineering materials and their physical and mechanical properties reflect this. Thus a plastic may be employed as a medical device because it possesses physical and mechanical properties suitable for use in a biological environment. However, until recently little attention was paid to the biological properties of these materials. This has resulted in a number of problems with current device materials as a result of adverse biological reactions. Silicone rubbers have been shown to leach toxic silicones when implanted, polyurethanes have been found to degrade by macrophage attack and natural rubbers have caused severe allergic reactions. In addition, PVC, a widely used polymer for medical devices, often contains large quantities of the plasticiser bis-(2-ethylhexyl)phthalate and many studies now show this to be toxic. It is clear, therefore, that many materials possess properties which render them unsuitable for use in biological applications.

Previous attempts to prepare biocompatible materials have mimicked the surface of platelet cells which under normal circumstances exist in the blood without causing any adverse reactions. These cell membranes comprise a phospholipid bilayer with the phosphorylcholine group dominating the external membrane surface. It is believed this outer surface avoids adverse reaction with other biological components. Lipids containing phosphorylcholine groups have been coated on to the surface of device materials and bloodclotting studies showed that they rendered the surface more biocompatible (J A Hayward & D Chapman, Biomaterials, Vol. 5, 135, 1984). These phospholipids have also been used as plasticisers in commercial polymers and have again improved the biocompatibility of the base material (WO-A-87/02684). However these two approaches nevertheless possess disadvantages.

Coating the surface of a finished device has a number of problems, one being the difficulty in coating devices with complex shapes or multiple components; in practice a multi-component device can be impossible to coat. In addition the degree of biocompatibility is dependent on the quality of the coating and how strongly it is bound to the surface; thus defects or scratches in the coating will reduce its effectiveness. The use of a lipid as a plasticiser goes some way to overcome these problems, but the lipid is free to move through the material and can eventually leach out of the system. This can again lead to a reduction in the level of biocompatibility. The lipid also has in addition no mechanical strength and can therefore only be used to soften the base polymer.

We have now devised new blended polymeric materials which seek to overcome these disadvantages. The blends combine the desirable physical and/or mechanical properties of an engineering polymer with the biocompatible properties of a polymer bearing pendant zwitterionic, for example phosphoryl choline, groups.

The present invention accordingly provides a polymer blend comprising:

(A) a polymer bearing zwitterionic pendant groups; and (B) a polymer having desirable mechanical and/or physical properties.

The extent to which a polymer bearing zwitterionic pendant groups (A) renders a further polymer biocompatible in a blend may be assessed as a combination of factors such as reduction in the extent to which the blend causes blood platelet activation and protein adsorption, (for instance as judged by absorption of fibrinogen from human plasma).

(A) Polymer Bearing Zwitterionic Pendant Groups

The polymer bearing zwitterionic pendant groups may be either a homopolymer or a copolymer. Preferably it is a polymer of residues of one or more radically polymerisable monomers, more preferably ethylenically unsaturated monomers. Preferably the polymer bears zwitterionic pendant groups by virtue of one of the starting monomers from which it is produced carrying such a group. Instead the zwitterionic group may be introduced onto a preformed polymer, for instance by reactions such as are disclosed in EP-A-0157469, WO-A-9113639, WO-A-9207858 or WO-A-9305081. The polymer may be a condensation polymer, for instance a polyurethane or a polyester. Again the zwitterionic group is present on the polymer either by incorporation as a pendant group on one of the starting monomers or by post-reaction of a preformed polymer. Polyurethanes are described in WO-A-8602933 and WO-A-89305081 and polyesters and described in WO-8800956.

Preferably the zwitterionic group is a group X as defined below.

Preferably the polymer is a copolymer of a comonomer containing a zwitterionic group and a comonomer containing an alkyl, usually a hydrophobic group, a reactive functional group, or an ionic group. The presence of residues of such comonomers may serve to improve the compatability of the polymer (A) for the polymer (B) in the blend of the present invention. Copolymers containing residues of a comonomer which contain a hydrophobic group are particularly preferred.

As examples of comonomers containing as hydrophobic groups, mention may be made of comonomers containing as pendant groups alkyl groups or fluoroalkyl groups, optionally having one or more etheric oxygen atoms interrupting the carbon chain, and optionally containing one or more carbon-carbon double or triple ones. Alternatively such comonomers may contain as pendant groups siloxane groups, preferably containing from 1 to 50, more preferably 5 to 30, silicon atoms.

The nature of such hydrophobic groups may be chosen for comparability with polymer (B). For example comonomers containing a hydrophobic fluoroalkyl group are particularly suitable for blending with fluoropolymer such as polyvinylidene fluoride (PVDF).

Alternatively, the polymer may comprise residues of a monomer containing both a zwitterionic group and such a hydrophobic group.

Preferably, such a hydrophobic group is an alkyl or fluoroalkyl group, optionally containing one or more carbon-carbon double or triple bonds. More preferably, the hydrophobic group does not contain any ethylenic unsaturation.

Alternatively, or in addition, such copolymers may further comprise residues of a comonomer containing a reactive functional group or an ionic group. Such reactive groups may serve to crosslink the copolymer (A) and/or bind the copolymer (A) to the polymer (B) having desirable physical and/or mechanical properties. In addition such reactive groups may provide reactive moieties at the surface of the blend. Use of a comonomer of containing ionic groups may serve to improve the miscability of the polymer (A) with polymer (B) where polymer (B) itself bears ionically charged groups.

In addition, the polymer (A) may further comprise residues of one or more diluent comonomers.

Monomers and comonomers of ethylenically unsaturated monomers which may be used in the preferred polymers (A) will now be described in more detail.

It is to be understood that throughout the specification (alk)acrylate, (alk)acrylic and (alk)acrylamide mean acrylate or alkacrylate, acrylic or alkacrylic and acrylamide or alkacrylamide respectively.

Preferably unless otherwise stated alkacrylate, alkacrylic and alkacrylamide groups contain from 1 to 4 carbon atoms in the alkyl group thereof and are most preferably methacrylate, methacrylic or methacrylamide groups. Similarly (meth)acrylate, (meth)acrylic and (meth)acrylamide shall be understood to mean acrylate or methacrylate, acrylic or methacrylic and acrylamide or methacrylamide respectively.

A.1. Monomers Containing a Zwitterionic Group

Preferred comonomers which contain a zwitterionic group are of general formula (I)

$$Y\text{—}B\text{—}X \quad (I)$$

wherein B is a straight or branched alkylene, oxaalkylene or oligo-oxaalkylene chain optionally containing one or more fluorine atoms up to and including perfluorinated chains or, if X contains a carbon-carbon chain between B and the zwitterionic moiety or if Y contains a terminal carbon atom bonded to B, a valence bond;

X is a zwitterionic group and

Y is an ethylenically unsaturated polymerisable group selected from

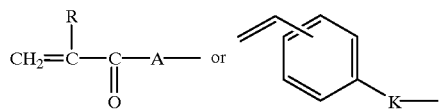

wherein:

R is hydrogen or a $C_1$–$C_4$ alkyl group;

A is —O— or —$NR^1$— where $R^1$ is hydrogen or a $C_1$–$C_4$ alkyl group or $R^1$ is —B—X where B and X are as defined above; and K is a group —$(CH_2)_pOC(O)$—, —$(CH_2)_pC(O)O$—, —$(CH_2)_pOC(O)O$—, —$(CH_2)_pNR^2$—, —$(CH_2)_pNR^2C(O)$—, —$(CH_2)_pC(O)NR^2$—, —$(CH_2)_pNR^2C(O)O$—, —$(CH_2)_pOC(O)NR^2$—, —$(CH_2)_pNR^2C(O)NR^2$—, (in which the groups $R^2$ are the same or different) —$(CH_2)_pO$—, —$(CH_2)_pSO_3$—, or, optionally in combination with B, a valence bond and p is from 1 to 12 and $R^2$ is hydrogen or a $C_1$–$C_4$ alkyl group.

The proviso on whether B may be a valence bond ensures that the zwitterionic moiety in X is not directly bonded to a heteroatom, such as an oxygen or nitrogen atom in Y.

Preferred monomers containing a zwitterionic group are therefore of general formula (II) or (III).

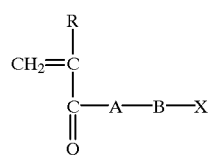

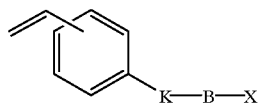

where R, A, B, K and X are as defined with reference to formula (I).

Preferably in the compounds of formula (II) R is hydrogen, methyl, or ethyl, more preferably methyl, so that (II) is an acrylic acid, methacrylic acid or ethacrylic acid derivative.

In the compounds of formula (III) K may be a valence bond and B a group, K may be a group and B a valence bond, both K and B may be groups, or K and B may together be a valence bond. Preferably B is a group where K is a valence bond.

Where K is a group then preferably p is from 1 to 6, more preferably 1,2 or 3 and most preferably p is 1. When K is a group —$(CH_2)_pNR^2$—, —$(CH_2)_pNR^2C(O)$—, —$(CH_2)_pC(O)NR^2$—, —$(CH_2)_pNR^2C(O)O$—, —$(CH_2)_pOC(O)NR^2$— or —$(CH_2)_pNR^2C(O)NR^2$— then $R^2$ is preferably hydrogen, methyl or ethyl, more preferably hydrogen.

In the compounds of formula (III) preferably the vinyl group is para to the group —K—B—X.

Preferably B is:

an alkylene group of formula —$(CR^3_2)_a$—, wherein the groups —$(CR^3_2)$— are the same or different, and in each group —$(CR)^3_2$— the groups $R^3$ are the same or different and each group $R^3$ is hydrogen, fluorine or $C_{1-4}$ alkyl or fluoroalkyl, preferably hydrogen, and a is from 1 to 12, preferably 1 to 6;

an oxaalkylene group such as alkoxyalkyl having 1 to 6 carbon atoms in each alkyl moiety, more preferably —$CH_2O(CH_2)_4$—; or an oligo-oxaalkylene group of formula —$[(CR^4_2)_bO]_c(CR^4_2)_b$— where the groups —$(CR^4_2)$— are the same or different and in each group —$(CR^4_2)$— the groups $R^4$ are the same or different and each group $R^4$ is hydrogen, fluorine or $C_{1-4}$ alkyl or fluoroalkyl, preferably hydrogen, and b is from 1 to 6, preferably 2 or 3 and c is from 2 to 11, preferably 2 to 5; or if X contains a carbon-carbon chain between B and the centre of permanent positive charge or if Y contains a terminal carbon atom, a valence bond.

Preferred groups B include alkylene, oxaalkylene and oligo-oxaalkylene groups of up to 12 carbon atoms optionally containing one or more fluorine atoms.

In compounds of formula (III) it is preferred that K and B contain up to 12 carbon atoms in total.

Preferred zwitterionic groups for instance which are groups on ethylenically unsaturated monomer YBX are groups in which the cationic moiety is based on a quaternary ammonium group and the anionic moiety is based on a phosphate group. Preferred zwitterionic groups are ammonium phosphate ester zwitterionic groups. Usually the cationic is located aet the end of pendant group X distant from B. Most preferred are the groups of formula (IVA), (IVB), (IVC), (IVD) and (IVE) as defined below: monomers containing such groups may be used alone in homopolymers or in combination with further comonomers to provide a copolymer. Of these groups (IVB) are particularly preferred.

In addition, groups of formula (VA), (VB) and (VC) are preferred as monomers containing both a zwitterionic group and a hydrophobic alkyl, fluoroalkyl or siloxane group.

The groups of formula (IVA) are:

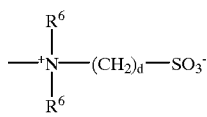

(IVA)

where the groups $R^6$ are the same or different and each is hydrogen or $C_{1-4}$ alkyl and d is from 2 to 4.

Preferably the groups $R^6$ are the same. It is also preferable that at least one of the groups $R^6$ is methyl, and more preferable that the groups $R^6$ are both methyl.

Preferably d is 2 or 3, more preferably 3.

When X is a group of formula (IVA) preferably B is a group of formula $-(CR^3{}_2)-$ or $-(CR^3{}_2)_2-$, eg. $-(CH_2)-$ or $-(CH_2CH_2)-$.

The groups of formula (IVB) are:

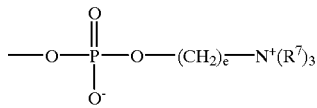

(IVB)

where the groups $R^7$ are the same or different and each is hydrogen or $C_{1-4}$ alkyl, and e is from 1 to 4.

Preferably the groups $R^7$ are the same. It is also preferable that at least one of the groups $R^7$ is methyl, and more preferable that the groups $R^7$ are all methyl.

Preferably e is 2 or 3, more preferably 2.

When X is a group of formula (IVB) preferably B is a group of formula $-(CR^3{}_2)-$ or $-(CR^3{}_2)_2-$, eg. $-(CH_2)-$ or $-(CH_2CH_2)-$.

The groups of formula (IVC) are:

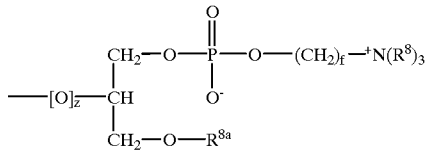

(IVC)

wherein the groups $R^8$ are the same or different and each is hydrogen or $C_{1-4}$ alkyl, $R^{8a}$ is hydrogen or, more preferably, a group $-C(O)B^1R^{8b}$ where $R^{8b}$ is hydrogen or methyl, preferably methyl, $B^1$ is a valence bond or straight or branched alkylene, oxaalkylene or oligo-oxaalkalyene group, and f is from 1 to 4; and if B is other than a valence bond Z is 1 and if B is a valence bond Z is O, if X is directly bonded to an oxygen or nitrogen atom and otherwise Z is 1.

Preferably the groups $R^8$ are the same. It is also preferable that at least one of the groups $R^8$ is methyl, and more preferable that the groups $R^8$ are all methyl.

Preferably f is 1 or 2, more preferably 2.
Preferably $B^1$ is:
a valence bond;
an alkylene group of formula $-(CR^{3a}{}_2)_{aa}-$, wherein the groups $-(CR^{3a}{}_2)-$ are the same or different, and in each group $-(CR^{3a}{}_2)-$ the groups $R^{3a}$ are the same or different and each group $R^{3a}$ is hydrogen or $C_{1-4}$ alkyl, preferably hydrogen, and aa is from 1 to 12, preferably 1 to 6;
an oxaalkylene group such as alkoxyalkyl having 1 to 6 carbon atoms in each alkyl moiety, more preferably $-CH_2O(CH_2)_4-$; or
an oligo-oxaalkylene group of formula $-[(CR^{4a}{}_2)_{ba}O]_{ca}-$ where the groups $-(CR^{4a}{}_2)-$ are the same or different and in each group $-(CR^{4a}{}_2)-$ the groups $R^{4a}$ are the same or different and each group $R^{4c}$ is hydrogen or $C_{1-4}$ alkyl, preferably hydrogen, and ba is from 1 to 6, preferably 2 or 3, and ca is from 1 to 12, preferably 1 to 6.

Preferred groups $B^1$ include a valence bond and alkylene, oxaalkylene and oligo-oxaalkylene groups of up to 12 carbon atoms.

Preferably B and $B^1$ are the same.

When X is a group of formula (IVC) preferably B is a group of formula $-[(CR^4{}_2CR^4{}_2)_cO_b]CR^4{}_2CR^4{}_2-$, eg. $-(CH_2CH_2O)_c(CH_2CH_2)-$.

The groups of formula (IVD) are:

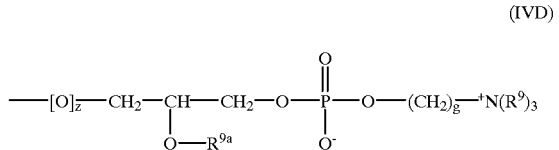

(IVD)

wherein the groups $R^9$ are the same or different and each is hydrogen or $C_1-C_4$ alkyl, $R^{9a}$ is a hydrogen or, more preferably, a group $-C(O)B^2R^{9b}$, $R^{9b}$ is hydrogen or methyl, preferably methyl, $B^2$ is a valence bond or a straight or branched alkylene, oxaalkylene or oligo-oxaalkylene group, and g is from 1 to 4; and if B is other than a valence bond Z is 1 and if B is a valence bond Z is O if X is directly bonded to an oxygen or nitrogen atom and otherwise Z is 1.

Preferably the groups $R^9$ are the same. It is also preferable that at least one of the groups $R^9$ is methyl, and more preferable that the groups $R^9$ are all methyl.

Preferably g is 1 or 2, more preferably 2.
Preferably $B^2$ is:
a valence bond;
an alkylene group of formula $-(CR^{3b}{}_2)_{ab}-$, wherein the groups $-(CR^{3b}{}_2)-$ are the same or different, and in each group $-(CR^{3b}{}_2)-$ the groups $R^{3b}$ are the same of different and each group $R^{3b}$ is hydrogen or $C_{1-4}$ alkyl, preferably hydrogen, and ab is from 1 to 12, preferably 1 to 6;
an oxaalkylene group such as alkoxyalkyl having 1 to 6, carbon atoms in each alkyl moiety, more preferably $-CH_2O(CH_2)_4-$; or
an oligo-oxaalkylene group of formula $-[(CR^{4b}{}_2)_{bb}O]_{cb}-$ where the groups $-(CR^{4b}{}_2)-$ are the same or different and in each group $-(CR^{4b}{}_2)-$ the groups $R_{4b}$ are the same or different and each group $R^{4b}$ is hydrogen or $C_{1-4}$ alkyl, preferably hydrogen, and bb is from 1 to 6, preferably 2 or 3, and cb is from 1 to 12, preferably 1 to 6.

Preferred groups $B^2$ include a valence bond and alkylene, oxalkylene and oligo-oxalkylene groups of up to 12 carbon atoms.

Preferably B and $B^2$ are the same.

When X is a group of formula (IVD) preferably B is a group of formula $—[(CR^4{}_2CR^4{}_2)_bO]_cCR^4{}_2CR^4{}_2—$, eg. $—(CH_2CH_2O)_cCH_2CH_2—$.

The groups of formula (IVE) are:

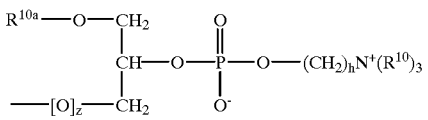

(IVE)

wherein the groups $R_{10}$ are the same or different and each is hydrogen or $C_{1-4}$ alkyl, $R^{10a}$ is hydrogen or, more preferably, a group $—C(O)B^3R^{10b}$ where $R^{10b}$ is hydrogen or methyl, preferably methyl, $B^3$ is a valence bond or a straight or branched alkylene, oxaalkylene or oligo-oxaalkylene group, and h is from 1 to 4; and if B is other than a valence bond Z is 1 and if B is a valence bond Z is 0 if X is directly bonded to the oxygen or nitrogen and otherwise Z is 1.

Preferably the groups $R^{10}$ are the same. It is also preferable that at least one of the groups $R^{10}$ is methyl, and more preferable that the groups $R^{10}$ are all methyl.

Preferably h is 1 or 2, more preferably 2.

Preferably $B^3$ is:

a valence bond;

an alkylene group of formula $—(CR^{3c}{}_2)_{ac}—$, wherein the groups $—(CR^{3c}{}_2)—$ are the same or different, and in each group $—(CR^{3c}{}_2)—$ the groups $R^{3c}$ are the same or different and each group $R^{3c}$ is hydrogen or $C_{1-4}$ alkyl, preferably hydrogen, and ac is from 1 to 12, preferably 1 to 6;

an oxaalkylene group such as alkoxyalkyl having 1 to 6 carbon atoms in each alkyl moiety, more preferably $—CH_2O(CH_2)_4—$; or an oligo-oxaalkylene group of formula $—[(CR^{4c}{}_2)_{bc}O]_{cc}—$ where the groups $—(CR^{4c}{}_2)—$ are the same or different and in each group $—(CR^{4c}{}_2)—$ the groups $R^{4c}$ are the same or different and each group $R^{4c}$ is hydrogen or $C_{1-4}$ alkyl, preferably hydrogen, and bc is from 1 to 6, preferably 2 or 3, and cc is from 1 to 12, preferably 1 to 6.

Preferred groups $B^3$ include a valence bond and alkylene, oxaalkylene and oligo-oxaalkylene groups of up to 12 carbon atoms.

Preferably B and $B^3$ are the same.

When X is a group of formula (IVE) preferably B is a group of formula $—[(CR^4{}_2CR^4{}_2)_bO]_cCR^4{}_2CR^4{}_2—$, eg. $—(CH_2CH_2O)_cCH_2CH_2—$.

Further zwitterionic groups are of formula (VA), (VB) and (VC). These groups also contain an alkyl, fluoroalkyl or siloxane group. Monomers containing such a group are therefore particularly suitable for use in polymers without separate comomoners containing a hydrophobic group.

The groups of formula (VA) are:

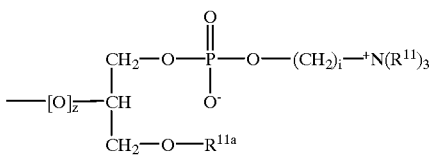

(VA)

wherein the groups $R^{11}$ are the same or different and each is hydrogen or $C_{1-4}$ alkyl, $R^{11a}$ is either (a) a group $—[C(O)]_{vw}(CR^{11b}{}_2)_{ww}(SiR_{11c2})(OSiR^{11c}{}_2)_{vv}R^{11c}$ in which each group $R^{11b}$ is the same or different and is hydrogen or alkyl of 1 to 4 carbon atoms, each group $R^{11c}$ is the same or different and is alkyl of 1 to 4 carbon atoms or aralkyl, for example benzyl or phenethyl, vw is 0 or 1, ww is from 0 to 6 with the proviso that vw and ww are not both 0, and vv is from 0 to 49;

(b) a group of formula $—C(O)B^4—R^{11d}$, in which $R^{11d}$ is hydrogen or methyl, $B^4$ is a valence bond or straight or branched alkylene, oxaalkylene or oligo-oxaalkalyene group optionally containing one or more fluorine atoms, and containing from 6 to 24, preferably 6 to 18 carbon atoms; i is from 1 to 4; and if B is other than a valence bond Z is 1 and if B is a valence bond Z is 0 if X is directly bonded to an oxygen or nitrogen atom and otherwise Z is 1.

Preferably the groups $R^{11}$ are the same. It is also preferable that at least one of the groups $R^{11}$ is methyl, and more preferable that the groups $R^{11}$ are all methyl.

Preferably i is 1 or 2, more preferably 2.

Where $R^{11a}$ is a siloxane group as defined in (a) above, each group $(CR^{11b}{}_2)$ may be the same or different, preferably the same, and preferably each group $R^{11b}$ is hydrogen. Preferably ww is from 2 to 4, and is most preferably 3 when vw is 0 or 2 when vw is 1. Each group $(SiR^{11c}{}_2)$ may be the same or different, preferably the same, and preferably each group $R^{11c}$ is methyl. Preferably vv is from 4 to 29.

Preferably the group $R^{11a}$ is a group $—C(O)B^4R^{11d}$ as defined above. In such a case, preferably $B^4$ is:

a valence bond;

an alkylene group of formula $—(CR^{3d}{}_2)_{ad}—$, wherein the groups $—(CR^{3d}{}_2)—$ are the same or different, and in each group $—(CR^{3d}{}_2)—$ the groups $R^{3d}$ are the same or different and each group $R^{2d}$ is hydrogen, fluorine or $C_{1-4}$ alkyl or fluoroalkyl, preferably hydrogen or fluorine, and ad is from 1 to 24, preferably 6 to 18;

an oxaalkylene group such as alkoxyalkyl having 1 to 6 carbon atoms -and optionally one or more fluorine atoms in each alkyl moiety, or an oligo-oxalkylene group of formula $—[(CR^{4d}{}_2)_{bd}O]_{cd}—$ where the groups $—(CR^{4d}{}_2)—$ are the same or different and in each group $—(CR^{4d}{}_2)—$ the groups $R^{4d}$ are the same or different and each group $R^{4d}$ is hydrogen, fluorine or $C_{1-4}$ alkyl or fluoroalkyl, preferably hydrogen or fluorine, and bd is from 2 to 6, preferably 3 or 4, and cd is from 1 to 12, preferably 1 to 6.

In one embodiment B and B may be the same.
The groups of formula (VB) are:

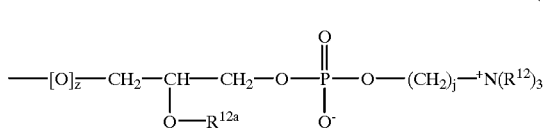

VB wherein the groups $R^{12}$ are the same or different and each is hydrogen or $C_1$–$C_4$ alkyl, $R^{12a}$ is either (a) a group —[C(O)]$_{tu}$ (CR$^{12b}_2$)$_{uu}$ (SiR$^{12c}_2$) (OSiR$^{12c}_2$)$_{tt}$ $R^{12c}$ in which each group $R^{12b}$ is the same or different and is hydrogen or alkyl of 1 to 4 carbon atoms, each group $R^{12c}$ is the same or different and is alkyl of 1 to 4 carbon atoms or aralkyl, for example benzyl or phenethyl, tu is 0 or 1, uu is from 0 to 6, with the proviso that tu and uu are not both 0, and tt is from 0 to 49; or (b) a group of formula —C(O)B$^5$—R$^{12d}$, in which $R^{12b}$ is hydrogen or methyl, B$^5$ is a valence bond or a straight or branched alkylene, oxaalkylene or oligo-oxaalkylene group optionally containing one or more fluorine atoms and from 6 to 24 carbon atoms, more preferably 6 to 18 carbons atoms, j is from 1 to 4; and if B is other than a valence bond, Z is 1 and if B is a valence bond Z is 0 if X is directly bonded to an oxygen or nitrogen atom and otherwise Z is 1.

Preferably the groups $R^{12}$ are the same. It is also preferable that at least one of the groups $R^{12}$ is methyl, and more preferable that the groups $R^{12}$ are all methyl.

Preferably j is 1 or 2, more preferably 2.

Where $R^{12a}$ is a siloxane group as defined in (a) above, each group (CR$^{12b}_2$) may be the same or different, preferably the same, and preferably each group $R^{12b}$ is hydrogen. Preferably uu is from 2 to 4, and is most preferably 3 when tu is 0 or 2 when tu is 1. Each group (SiR$^{12c}_2$) may be the same or different, preferably the same, and preferably each group $R^{12c}$ is methyl. Preferably tt is from 4 to 29.

Preferably the group $R^{12a}$ is a group —C(O)B$^4$R$^{12d}$ as defined above. In such a case, preferably B$^5$ is:

a valence bond;

an alkylene group of formula —(CR$^{3e}_2$)$_{ae}$—, wherein the groups —(CR$^{3e}_2$)— are the same or different, and in each group —(CR$^{3e}_2$)— the groups $R^{3e}$ are the same of different and each group $R^{3e}$ is hydrogen, fluorine or $C_{1-4}$ alkyl, or fluoroalkyl, preferably hydrogen or fluorine, and ae is from 1 to 24, preferably 6 to 18;

an oxaalkylene group such as alkoxyalkyl having 1 to 6 carbon atoms and optionally one or more fluorine atoms in each alkyl moiety; or an oligo-oxaalkylene group of formula —[(CR$^{4e}_2$)$_{be}$O]$_{ce}$— where the groups —(CR$^{4e}_2$)— are the same or different and in each group —(CR$^{4e}_2$)— the groups $R^{4e}$ are the same or different and each group $R^{4e}$ is hydrogen, fluorine or $C_{1-4}$ alkyl or fluoroalkyl, preferably hydrogen or fluorine, and be is from 2 to 6, preferably 3 or 4, and ce is from 1 to 12, preferably 1 to 6.

In one embodiment B and B$^5$ may be the same.
The groups of formula (VC) are:

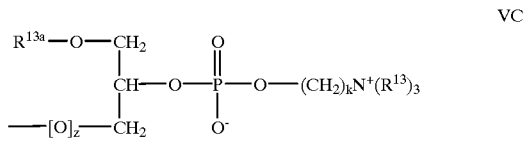

VC where the groups $R^{13}$ are the same or different and each is hydrogen or $C_{1-4}$ alkyl, $R^{13a}$ is either (a) a group —[C(O)]$_{rs}$(CR$^{13b}_2$)$_{ss}$ (SiR$^{13c}_2$) (OSiR$^{13c}_2$)$_{rr}$ $R^{13c}$ in which each group $R^{13b}$ is the same or different and is hydrogen or alkyl of 1 to 4 carbon atoms, each group $R^{13c}$ is the same or different and is alkyl of 1 to 4 carbon atoms or aralkyl, for example benzyl or phenethyl, rs is 0 or 1, ss is from 0 to 6, with the proviso that rs and ss are not both 0, and rr is from 0 to 49; or (b) a group of formula —C(O)B$^6$—R$^{13d}$, in which $R^{13a}$ is hydrogen or methyl, B$^6$ is a valence bond or a straight or branched alkylene, oxaalkylene or oligo-oxaalkylene group optionally containing one or more fluorine atoms and from 6 to 24, more preferably 6 to 18 carbon atoms and k is from 1 to 4; and if B is other than a valence bond, Z is 1 and if B is a valence bond Z is 0 if X is directly bonded to an oxygen or nitrogen atom and otherwise Z is 1.

Preferably the groups $R^{13}$ are the same. It is also preferable that at least one of the groups $R^{13}$ is methyl, and more preferable that the groups $R^{13}$ are all methyl.

Preferably k is 1 or 2, more preferably 2.

Where $R^{13a}$ is a siloxane group as defined in (a) above, each group (CR$^{13b}_2$) may be the same or different, preferably the same and preferably each group $R^{13b}$ is hydrogen. Preferably ss is from 2 to 4, and is most preferably 3 when rs is 0 or 2 when rs is 1. Each group (SiR$^{13c}_2$) may be the same, or different, preferably the same, and preferably each group $R^{13c}$ is methyl. Preferably rr is from 4 to 29.

Preferably the group $R^{13a}$ is a group —C(O)B$^6$R$^{13d}$ as defined above. In such a case, preferably B$^6$ is:

a valence bond;

an alkylene group of formula —(CR$^{3f}_2$)$_{af}$—, wherein the groups —(CR$^{3f}_2$)— are the same or different, and in each group —(CR$^{3f}_2$)— the groups $R^{3f}$ are the same or different and each group $R^{3f}$ is hydrogen, fluorine or $C_{1-4}$ alkyl or fluoroalkyl, preferably hydrogen or fluorine, and is from 1 to 24, preferably 6 to 18;

an oxaalkylene group such as alkoxyalkyl having 1 to 6 carbon atoms and optionally one or more fluorine atoms in each alkyl moiety; or an oligo-oxaalkylene group of formula —[(CR$^{4f}_2$)$_{bf}$O]$_{cf}$— where the groups —(CR$^{4f}_2$)— are the same or different and in each group —(CR$^{4f}_2$)— the groups $R^{4f}$ are the same or different and each group $R^{4f}$ is hydrogen, fluorine or $C_{1-4}$ alkyl or fluoroalkyl, preferably hydrogen or fluorine, and bf is from 2 to 6, preferably 3 or 4, and cf is from 1 to 12, preferably 1 to 6.

In one embodiment B and B$^6$ may be the same.

Particular examples of preferred monomers containing a zwitterionic group are 2-(methacryloyloxy)ethyl-2'-(trimethylammonium)ethyl phosphate inner salt and 1[4(4'-vinylbenzyloxy)butane]-2'(trimethylammonium)ethyl phosphate inner salt.

Monomers containing a zwitterionic group such as those of formula (II) and (III) may be prepared by conventional techniques using known reactions, for example using a suitable substituted alkyl (alk)acrylate or suitable substituted styrene as precursor. Examples of suitable substituted alkyl (alk)acrylates include dimethylaminoethyl(meth)acrylate and 2-hydroxyethyl(meth)acrylate.

Monomers of formula (II) or (III) containing a group of formula (IVA) or (IVB) may be prepared as described in the Reference Examples herein or by analogous known methods.

Monomers of formula (II) or (III) containing a group of formula (IVC) in which $R^{8a}$ is —C(O)B$^1$R$^{8b}$ may be prepared by selective acylation of glycerophosphorylcholine or analogues thereof at the primary hydroxyl group with an activated acid derivative such as an acid anhydride O(C(O)B$^1$R$^{8b}$)$_2$ or an acid halide R$^{8b}$B$^1$COHAl where B$^1$ and R$^{8b}$ are as defined above and Hal is halogen, followed by acylation of the secondary hydroxyl group with an appropriate acylating agent, for example methacryloyl chloride. Purification, for example by column chromatography on a suitable support, may be performed after each acylation or after the second acylation only. Suitable activated acid derivatives include acid anhydrides, acid halides, reactive esters and imidazolides. The acylations may be performed in a suitable anhydrous, aprotic solvent, for example N,N-dimethylformamide, optionally in the presence of a suitable non-nucleophilic base, for example triethylamine.

Alternatively, the primary alcohol group in glycerophosphoryl choline or an analogue thereof may be blocked by reaction with a suitable protecting group reagent, for example t-butyldimethylsilyl chloride, under standard conditions and the secondary hydroxy group then treated with an acylating agent such as methacryloyl chloride. The t-butyldimethylsilyl protecting group may be removed by treatment with a dilute organic or mineral acid, for example p-toluene sulphonic acid, hydrochloric acid or with tetra-butylammonium fluoride. The deblocked primary hydroxyl group may then be treated with an activated acid derivative such as an acid anhydride O(C(O)B$^1$R$^{8b}$)$_2$ or acid halide R$^{8b}$B$^1$COHal where B$^1$ and R$^{8b}$ are as defined above, and Hal is halogen.

Analogues of glycerophosphorylcholine (compounds of formula (II) or (III) containing a group (IVD) where $R^{8a}$ is hydrogen) may be prepared by reaction of phosphorus oxychloride with a bromoalcohol in an inert aprotic solvent, such as dichloromethane, to give a bromoalkylphosphorodichloridate. The dichloro derivative thus produced may then be treated with an appropriately protected glycerol derivative, for example 2,2-dimethyl 1,3-dioxolane-4-methanol, in the presence of a base, for example triethylamine, followed by acid hydrolysis to give a bromoalkylphosphoro-glycerol derivative. This may then be treated with an amine NR$^8$$_3$, where R$^8$ is as defined above, for example trimethylamine, to generate the glycerophosphorylcholine analogue. This preparation is depicted in the following scheme.

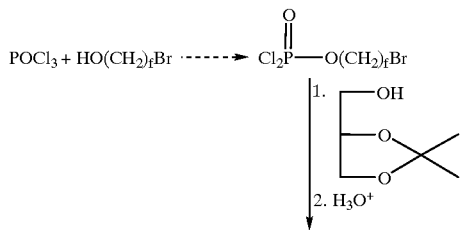

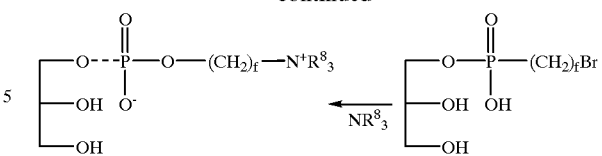

where $R^8$ and f are as defined in relation to groups of formula (IVC).

Monomers of formula (II) or (III) containing a group of formula (IVD) in which $R^{9a}$ is —C(O)B$^2$R$^{9b}$ may be prepared by the selective acylation of glycerophosphorylcholine or an analogue thereof at the primary hydroxyl group with for example, methacryloyl chloride followed by reaction at the secondary hydroxyl group using an activated acid derivative, such as an acid halide O(C(O)B$^2$R$^{9b}$)$_2$ or an acid halide R$^{9b}$B$^2$COHal, where B$^2$ and R$^{9b}$ are as defined above and Hal is halogen. The intermediates and final products may be purified, as necessary using column chromatography. Optionally, protecting group strategy, similar to that outlined above in relation to production of monomers containing a group of formula (IVC) may be employed.

Monomers of formula (II) or (III) containing a group of formula (IVE) may be prepared in an analogous manner to monomers containing groups of formula (IVD) or (IVE).

Monomers of formula (II) or (III) containing a group of formula (VA), (VB) or (VC) may be prepared by direct analogy with methods described for monomers containing groups of formula (IVC), (IVD) and (IVE) respectively.

A.2. Comonomers, for Instance Containing a Hydrophobic, Reactive or Ionic Group

The polymer (A) containing pendant zwitterionic groups preferably comprises residues of a further comonomer containing a hydrophobic, functional or ionic group as well as the residues of the comonomer containing a zwitterionic group. The presence of such addition comonomer residues may modify the properties of the copolymer to improve its compatibility with the polymer (B) in the blends of the invention.

It will be appreciated that in some circumstances it may be desirable to use a combination of different comonomers containing different types of groups. Preferably a comonomer of type a), b) and/or c) as defined below or a combination of such comonomers is used, more preferably only one of comonomer types a), b) and c) is used.

A.2.a. Comonomers Containing an Alkyl, Fluoroalkyl or Siloxane Group

The comonomers containing an alkyl-based group for instance a hydrophobic group, or one which contains for instance a fluoroalkyl or siloxane group, are comonomers containing a) an alkyl group which group optionally contains one or more etheric oxygen atoms and optionally one or more carbon-carbon double or triple bonds for instance which has 6 or more carbon atoms, or b) a fluoroalkyl group, preferably of 6 or more carbon atoms, which group optionally contains one or more etheric oxygen atoms and optionally one or more carbon-carbon double or triple bonds, or c) a siloxane group, containing up to 50 silicon atoms, preferably in a linear chain.

Preferably the alkyl or fluoroalkyl groups contains up to 24 carbon atoms, for instance up to 18 carbon atoms.

Preferred comonomers containing an alkyl, fluoroalkyl or siloxane group are those of general formula (VI)

$$Y^1-Q \qquad \text{(VI)}$$

where $Y^1$ is an ethylenically unsaturated polymerisable group selected from

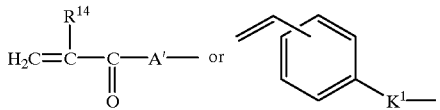

where $R^{14}$ is hydrogen or $C_1$–$C_4$ alkyl,

A' is —O— or —$NR^{15}$— where $R^{15}$ is hydrogen or a $C_1$–$C_4$ alkyl group or $R^{15}$ is a group Q;

$K^1$ is a group —$(CH_2)_lOC(O)$—, —$(CH)_lC(O)O$—, —$(CH_2)_lOC(O)O$—, —$(CH_2)_lNR^{16}$—, —$(CH_2)_lNR^{16}C(O)$—, —$(CH_2)_lC(O)NR^{16}$—, —$(CH_2)_lNR^{16}C(O)O$—, —$(CH_2)_lOC(O)NR^{16}$—, —$(CH_2)_lNR^{16}C(O)NR^{16}$— (in which the groups $R^{16}$ are the same or different), —$(CH_2)_lO$—, —$(CH_2)_lSO_3$—, a valence bond and l is from 1 to 12 and $R^{16}$ is hydrogen or a $C_1$–$C_4$ alkyl group; and Q is (a) a straight or branched alkyl, alkoxyalkyl or (oligo-alkoxy)alkyl chain containing, for instance preferably 6 to 24, carbon atoms unsubstituted or substituted by one or more fluorine atoms and optionally containing one or more carbon-carbon double or triple bonds; or (b) a siloxane group —$(CR^{16a}_2)_{qq}(SiR^{16b}_2)(OSiR^{16b}_2)_{pp}R^{16b}$ in which each group $R^{16a}$ is the same or different and is hydrogen or alkyl of 1 to 4 carbon atoms or aralkyl, for example benzyl or phenethyl, each group $R^{16}$ is alkyl of 1 to 4 carbon atoms, qq is from 1 to 6 and pp is from 0 to 49.

Preferred comonomers of formula (VI) bearing a group Q include those of formula (VII) and (VIII):

wherein:

$R^{14}$, A', $K^1$ and Q are as defined in relation to formula (VI).

Preferably in the compounds of formula VII) $R^{14}$ is hydrogen methyl or ethyl, more preferably methyl so that the compound of formula (VII) is preferably an acrylic acid, methacrylic acid or ethacrylic acid derivative.

In the compounds of formula (VIII) $K^1$ may for instance be a valence bond. Where $K^1$ is a group then preferably l is from 1 to 6, more preferably 1, 2 or 3 and most preferably l is 1. When $K^1$ is a group —$(CH_2)_lNR^{16}$—, —$(CH_2)_lOC(O)NR^{16}$—, —$(CH_2)_lNR^{16}C(O)O$—, —$(CH_2)_lNR^{16}C(O)$—, —$(CH_2)_lC(O)NR^{16}$— or —$(CH_2)_lNR^{16}C(O)NR^{16}$— then $R^{16}$ is preferably hydrogen, methyl or ethyl, more preferably hydrogen.

In the compounds of formula (VIII), preferably the vinyl group is para to the group —$K^1$—Q.

Preferably Q is an alkyl or fluoroalkyl group optionally containing one or more etheric oxygen atoms and optionally one or more carbon-carbon double or triple bonds. More preferably Q is:

an alkyl group of formula —$(CR^{17}_2)_mCR^{17}_3$, wherein the groups —$(CR^{17}_2)$— are the same or different, and in each group —$(CR^{17}_2)$— the groups $R^{17}$ are the same or different and each group $R^{17}$ is hydrogen, fluorine or $C_{1-4}$ alkyl or fluoroalkyl and m is from 5 to 23 if Q contains no fluorine atoms or from 1 to 23, preferably 5 to 23, if Q contains one or more fluorine atoms;

an alkoxyalkyl having 1 to 12 carbon atoms in each alkyl moiety; unsubstituted or substituted by one or more fluorine atoms; or an (oligo-alkoxyl) alkyl group of formula —$[(CR^{17}_2)_nO]_o(CR^{18}_2)_nR^{18}$ where the groups —$(CR^{18}_2)$— are the same or different and in each group —$(CR^{18}_2)$— the groups $R^{18}$ are the same or different and each group $R^{18}$ is hydrogen, fluorine or $C_{1-4}$ alkyl or fluoroalkyl and n is from 2 to 6, preferably 3 to 4, and o is from 1 to 12.

Alternatively, Q may be a group in which one or more of the alkyl or alkylene moieties in such an alkyl, alkoxyalkyl or (oligoalkoxy) alkyl group is replaced by a corresponding alkenyl, alkynyl, alkenylene or alkynylene moiety.

Preferred groups Q include alkyl, alkoxyalkyl and (oligoalkoxy)alkyl groups optionally containing one or more carbon-carbon double or triple bonds of 8 or more, more preferably 10 or more, even more preferably 12 or more, for instance 14 or more, such as 16 or more carbon atoms. Such groups may contain one or more fluorine atoms and be therefore fluoroalkyl derivatives. Preferably however, such groups do not contain any fluorine atoms.

Particularly preferred groups are straight chain alkyl or fluoroalkyl groups optionally containing one or more carbon-carbon double or triple bonds.

Where Q is a siloxane group, each group —$(CR^{16a}_2)$— may be the same or different, preferably the same, and preferably each group $R^{16a}$ is hydrogen. Preferably qq is from 2 to 4, and is most preferably 3. Each group —$(SiR^{16b}_2)$— may be the same or different, preferably the same, and preferably each group $R^{16b}$ is methyl. Preferably pp is from 4 to 29. Preferred comonomers where Q is a siloxane group are those of formula (VII).

In one specific embodiment the group Q does not contain any ethylenic unsaturation, i.e. any carbon-carbon double or triple bonds.

Particular examples of comonomers containing an alkyl, fluoroalkyl or siloxane group include: methylmethacrylate, butylmethacrylate, n-dodecyl methacrylate, octadecyl methacrylate, hexadecyl methacrylate, 1H,1H,2H,2H-heptadecafluorodecyl methacrylate, p-octyl styrene, p-dodecyl styrene and monomethacryloxypropyl terminated siloxanes n-Dodecyl methacrylate is particularly preferred.

Comonomers containing an alkyl or fluoroalkyl, which does not contain a carbon-carbon double or triple, bond, or a siloxane group such as those of formulae (VII) and (VIII) are commercially available or may be prepared by conventional techniques using known reactions.

In a second specific embodiment of such comonomers, the group Q does contain ethylene unsaturation, i.e. one or more carbon-carbon double or triple bonds. Such comonomers may for example contain a vinylic, divinylic, acetylenic or diacetylenic moiety. Comonomers containing acetylenic rather than vinylic unsaturation are in general preferred, especially those containing a single acetylenic group.

Comonomers which contain such an ethylenic unsaturated group, which does not react in the initial polymerisation reaction but which can be subsequently activated, are capable of providing crosslinking between linear polymer chains once the polymer is blended with a polymer (B). Such crosslinking through reaction of ethylenic or acetylenic pendant groups of the polymer A with other groups on polymer A molecules or on polymer B molecules may improve the stability of the blend and is typically formed by irradiation, for example with UV- or gamma-radiation. The crosslinking of such groups may be employed either alone or in addition to the use of a comonomer containing a reactive group as a crosslinkable comonomer as described below.

Particularly preferred crosslinkable comonomers containing a hydrophobic group are those of formula (VIIA) and (VIIIA).

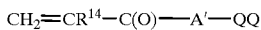

(VIIA)

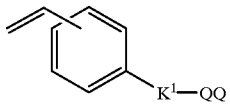

(VIIIA)

in which $R^{14}$, A' and $K^1$ are as hereinbefore defined and QQ is an alkynyl group containing 6 or more carbon atoms and one or two, preferably one, carbon-carbon triple bonds provided that the acetylenic moieties are not directly bonded to A' or $K^1$.

Amongst such comonomers it is preferred that QQ is a group containing from 6 to 24 carbon atoms., preferably 8 or more, more preferably 10 or more, even more preferably 12 or more, for instance 14 or more, such as 16 or more carbon atoms.

It is also preferred that the group QQ does not contain a terminal acetylenic moiety, i.e. a group —C≡CH.

A particularly preferred group QQ is 7-dodecynyl and a specific example of a compound of formula (VIIA) containing such a group is dodec-7-ynyl methacrylate.

The compounds of formula (VIIA) and (VIIIA) and other comonomers of formula (VII) and (VIII) containing an ethylenically unsaturated physisorbable group Q, may be prepared by analogy with known methods. Their preparation is illustrated by Reference Example 5.

A.2. (b) Comonomers bearing a reactive group

Preferred comonomers, which contain a reactive functional group capable of providing crosslinking within the polymer (A) or to the polymer (B) and/or providing reactive groups on the surface of the blend of the invention are of general formula (IX)

$$Y^2Q^1 \tag{IX}$$

where $Y^2$ is an ethylenically unsaturated polymerisable group selected from

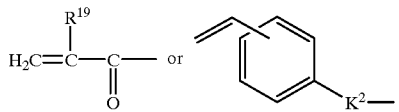

where $R^{19}$ is hydrogen or $C_1$-$C_1$-$C_4$ alkyl, $K^2$ is a group —$(CH_2)_qOC(O)$—, —$(CH)_qC(O)O$—, —$(CH_2)_qOC(O)O$—, —$(CH_2)_qNR^{20}$—, —$(CH_2)_qNR^{20}C(O)$—, —$(CH_2)_qC(O)NR^{20}$—, —$(CH_2)_qNR^{20}C(O)O$—, $(CH_2)_qOC(O)NR^{20}$—, —$(CH_2)_qNR^{20}C(O)NR^{20}$— (in which the groups $R_{20}$ are the same or different), —$(CH_2)_qO$—, or —$(CH_2)_qSO_3$—, or a valence bond and q is from 1 to 12 and $R^{20}$ is hydrogen or a $C_1$-$C_4$ alkyl group; and $Q^1$ is a reactive group capable of reacting to provide crosslinking within the polymer (A) or to the polymer (B) and/or providing a reactive group on the surface of the blend.

Preferred comonomers of formula (IX) bearing a reactive group $Q^1$ include those of formula (X) and (XI) defined below.

The compounds of formula (X) are:

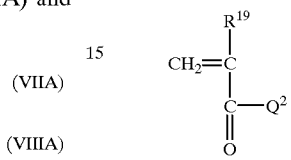

wherein:

$R^{19}$ is as defined with reference to formula (X), and.

$Q^2$ is a reactive group.

Preferably in the compounds of formula (X) $R^{19}$ is hydrogen, methyl or ethyl, more preferably methyl, so that the compound of formula (X) is preferably an acrylic acid, methacrylic acid or ethacrylic acid derivative.

Preferably $Q^2$ is hydrogen, or more preferably —OH or a group of the formula:

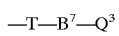

where T is —O—, or —$NR^{21}$— where $R^{21}$ is hydrogen, $C_1$-$C_4$ alkyl or a group —$B^7$—$Q^3$;

$B^7$ is a valence bond or, more preferably, a straight or branched alkylene, oxaalkylene or oligo-oxaalkylene chain; and $Q^3$ is a reactive group such as an aldehyde group or a silane or siloxane group containing one or more reactive substituents such as halogen, for example chlorine, or alkoxy, generally containing from 1 to 4 carbon atoms, for example methoxy or ethoxy, or, more preferably $Q^3$ is a hydroxyl, amino, carboxyl, epoxy, —$CHOHCH_2Hal$, (in which Hal is a halogen atom such as chlorine, bromine or iodine) succinimido, sulphonic acid esters such as tosylate and triflate, imidazole carbonyl-amino, or an optionally substituted triazine group.

Preferably $B^7$ is:

an alkylene group of formula —$(CR^{22}_2)_r$—, wherein the groups —$(CR^{22}_2)$— are the same or different, and in each group —$(CR^{22}_2)$— the groups $R^{22}$ are the same or different and each group $R^{22}$ is hydrogen or $C_{1-4}$ alkyl, preferably hydrogen, and r is from 1 to 12, preferably 1 to 6;

an oxaalkylene group such as alkoxyalkyl having 1 to 6 carbon atoms in each alkyl moiety; or an oligo-oxaalkylene group of formula —$[(CR^{23}_2)_sO]_t(CR^{23}_2)_s$— where the groups —$(CR^{23}_2)$— are the same or different and in each group —$(CR^{23}_2)$— the groups $R^{23}$ are the same or different and each group $R^{23}$ is hydrogen or $C_{1-4}$ alkyl, preferably hydrogen, and s is from 1 to 6, preferably 2 or 3, and t is from 1 to 11, preferably 1 to 5.

Preferred groups $B^7$ include alkylene, oxaalkylene and oligo-oxaalkylene groups of up to 12 carbon atoms.

Where $Q^3$ is a silane or siloxy group, preferably $B^7$ is an alkylene group of 1 to 6, preferably 2 to 4, more preferably 3 carbon atoms.

Particular examples of the group $B^7$ are —$CH_2$—, —$CH_2CH_2$— and —$(CH_2)_6$—.

The compounds of formula (XI) are:

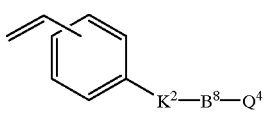

(XI)

wherein $K^2$ is as defined in relation to formula (IX) and;

$B^8$ is a straight of branched alkylene, oxaalkylene or oligo-oxaalkylene chain and $Q^4$ is a reactive group, for example an aldehyde group or a silane or siloxane group containing one or more reactive substituents such as halogen, for example chlorine, or alkoxy, generally containing from 1 to 4 carbon atoms, for example methoxy or ethoxy, or, more preferably, $Q^4$ is a hydroxyl, amino, carboxyl, epoxy, —$CHOHCH_2Hal$, (in which Hal is a halogen atom such as chlorine, bromine or iodine) succinimido, tosylate, triflate, imidazole carbonyl-amino or optionally substituted triazine group.

In the compounds of formula (XI) preferably the vinyl group is para to the group —$K^2$—$B^8$—$Q^4$.

$K^2$ may for instance be a valence bond. Where $K^2$ is a group then preferably q is from 1 to 6, more preferably 1,2 or 3 and most preferably q is 1. When $K^2$ is a group —$(CH_2)_qNR^{20}$—, —$(CH_2)_qOC(O)NR^{20}$—, —$(CH_2)_qNR^{20}C(O)O$—, —$(CH_2)_qNR^{20}C(O)$—, —$(CH_2)_qC(O)NR^{20}$— or —$(CH_2)_qNR^{20}C(O)NR^{20}$— then $R^{20}$ is preferably hydrogen, methyl or ethyl, more preferably hydrogen.

Preferably $B^8$ is:

an alkylene group of formula —$(CR^{24}_2)_u$—, wherein the groups —$(CR^{24}_2)$— are the same or different, and in each group —$(CR^{24}_2)$— the groups $R^{24}$ are the same of different and each group $R^{24}$ is hydrogen or $C_{1-4}$ alkyl, preferably hydrogen, and u is from 1 to 12, preferably 1 to 6;

an oxaalkylene group such as alkoxyalkyl having 1 to 6 carbon atoms in each alkyl moiety; or an oligo-oxaalkylene group of formula —$[(CR^{25}_2)_vO]_w(CR^{25}_2)_v$— where the groups —$(CR^{25}_2)$— are the same or different and in each group —$(CR^{25}_2)$— the groups $R^{25}$ are the same or different and each group $R^{25}$ is hydrogen or $C_{1-4}$ alkyl, preferably hydrogen, and v is from 1 to 6, preferably 2 or 3, and w is from 1 to 12, preferably 1 to 6.

Preferred groups B include alkylene, oxaalkylene and oligo-oxaalkylene groups of up to 12 carbon atoms. In one embodiment $B^8$ and $K^2$ contain together up to 12 carbon atoms.

Particular examples of comonomers bearing a reactive group include chloromethylstyrene, methacrylic acid, 2-aminoethylmethacrylate, 2,3-epoxypropyl methacrylate, 3-chloro-2-hydroxypropylmethacrylate, 2-methacryloyloxyethyl-dichloro-1,3,5-triazine, 3-chloro-2-hydroxy-propylmethacrylamide and glycidyl methacrylate and reactive methacrylate esters containing the group HetC(O)O— in which (Het) is a heterocyclic ring, for example benzotriazole or imidazole and reactive methacrylate esters containing a group $R^{16}OC(O)$— in which $R^{16}$ is a succinimido or pentafluorophenyl group.

Particularly preferred comonomers bearing reactive groups are 2-aminoethyl-methacrylate and 3-chloro-2-hydroxypropylmethacrylate.

Comonomers bearing a reactive group such as those of formula (X) or (XI), are commercially available or may be prepared by conventional techniques using known reactions.

Comonomers of formula (X), which are dichlorotriazine monomers may be prepared in known manner for example by reacting a substituted hydroxy-alkyl(alk)acrylate or aminoalkyl(alk)acrylate with trichlorotriazine in a suitable solvent and in the presence of a base.

Comonomers of formula (XI) which are reactive methacrylate esters in which the ester groups contains an imidazole group may be prepared in known manner by reacting a substituted hydroxyalkyl(alk)acrylate (e.g. 2-hydroxyethyl-(meth)acrylate), polyethylene-oxide (meth) acrylate or polypropyleneoxide (meth) acrylate with 1,1-carbonyl-diimidazole in a dry solvent. Analogous known methods may be used to prepare succinimido and pentafluorophenyl methacrylate esters of formula (X), by reaction with a reactive ester, acid halide or acid anhydride.

Reactive groups may provide points for the attachment of moieties such as ligands to the surface of the polymer blend.

Comonomers containing a reactive group, such as A compounds of formula (X) and (XI) may also be used as comonomers containing crosslinkable groups (i.e. coreactive groups), which react with other crosslinkable groups (or coreactive groups), either in the polymer (A) or the polymer (B).

Where comonomers containing a reactive group are used to provide such crosslinkable groups then the crosslinkable groups and/or the copolymerisation conditions will be chosen so that they will not crosslink when the comonomers are copolymerised; thus the polymerisation product will be an uncrosslinked linear copolymer which may be subsequently crosslinked after blending the copolymer with polymer (B) so as to improve the stability of the blend. When such crosslinking between linear polymer chains is employed the crosslinkage may be formed either between two such crosslinkable groups or between a crosslinkable group and a non-inert group mutually coreactive in a diluent comonomer residue (defined later). Such a crosslinkage may be formed either by direct reaction of the groups forming the crosslinkage or by reaction of these groups with a reactive bridging molecule for example a reactive gas, such as ammonia.

Residues of such comonomers may therefore be present in polymers which also contain residues of comonomers containing a hydrophobic group such as those of formula (VA), (VB) or (VC) or a comonomer containing an alkyl, fluoroalkyl or siloxane group, which is of formula (VII) or (VIII). Similarly residues of such comonomers may also be present in copolymers which contains residues of a compound containing an ionic group of formula (XIII) or (XIV) as defined below.

Preferred reactive comonomers which are used to crosslink the comonomer, are those of formula (X) or (XI) in which $Q^2$, or $Q^4$ contains a crosslinkable cinnamyl, epoxy, —$CHOHCH_2Hal$ (in which Hal is a halogen atom), methylol, silyl, an ethylenically unsaturated crosslinkable group, such as an acetylenic, diacetylenic, vinylic or divinylic group, or an acetoacetoxy or chloroalkyl sulfone, preferably chloroethyl sulphone, group.

Particular examples of comonomers bearing a group capable of crosslinking include methacrolein, cinnamyl methacrylate, 2,3-epoxypropyl methacrylate, 3-chloro-2-hydroxypropyl methacrylate, hydroxymethyl methacrylamide, 3-(trimethoxysilyl)propyl methacrylate, 2-acetoacetoxyethyl methacrylate, 3-(vinylbenzyl)-2-chloroethyl sulfone.

When a polymer (A) containing crosslinkable groups, is blended with a polymer (B) the polymer (A) is preferably in substantially uncrosslinked form. After blending and optionally after additional processing steps, crosslinking of crosslinkable groups may be performed to increase the strength and stability of the blend. Such crosslinking may for example be performed upon the final processed and shaped blend.

A.2. (c) Comonomers bearing an ionic group

Comonomers containing an ionic group may serve to improve the miscibility of the polymer (A) with the polymer (B), particularly if polymer (B) itself bears ionically charged groups.

Preferred comonomers bearing an ionic group art of general formula (XII)

$$Y^2\text{—}B^9\text{—}Q^5 \qquad (XII)$$

where $Y^2$ is an ethylenically unsaturated polymerisable group selected from

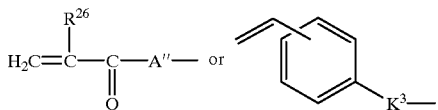

where $R^{26}$ is hydrogen or $C_1$–$C_4$ alkyl;

A" is —O— or —$NR^{27}$—, wherein $R^{27}$ is hydrogen or a $C_1$–$C_4$ alkyl group or $R^{27}$ is a group —$B^9$—$Q^5$;

$B^9$ is a valence bond, a straight or branched alkylene, oxaalkylene or oligo-oxaalkylene group;

$K^3$ is a group —$(CH_2)_xOC(O)$—, —$(CH)_xC(O)O$—, —$(CH_2)_xOC(O)O$—, —$(CH_2)_xNR^{28}$—, —$(CH_2)_xNR^{28}C(O)$—, —$(CH_2)_xC(O)NR^{28}$—, —$(CH_2)_xNR^{28}C(O)O$—, —$(CH_2)_xOC(O)NR^{28}$—, —$(CH_2)_xNR^{28}C(O)NR^{28}$— (in which the groups $R^{28}$ are the same or different), —$(CH_2)_xO$—, —$(CH_2)_xSO_3$—, a valence bond (optionally in combination with $B^9$) and x is from 1 to 12 and $R^{28}$ is hydrogen or a $C_1$–$C_4$ alkyl group;

$Q^5$ is an ionic group.

Preferred comonomers of formula (XII) are therefore those of formula (XIII) and (XIV):

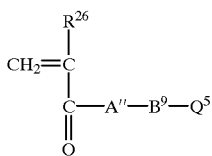

(XIII)

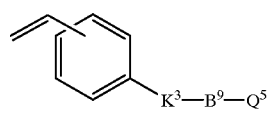

(XIV)

wherein:

$R^{26}$, A", $B^9$, $K^3$ and $Q^5$ are as defined in relation to formula (XII).

Preferably in the compounds of formula (XIII) $R^{26}$ is hydrogen, methyl or ethyl, more preferably methyl, so that the compound of formula (XIII) is preferably an acrylic acid, methacrylic acid or ethacrylic acid derivative.

In the compounds of formula (XIV), $K^3$ may for instance be a valence bond. Where $K^3$ is a group then x is preferably from 1 to 6, more preferably 1, 2 or 3 and most preferably x is 1. When $k^3$ is a group —$(CH_2)_xNR^{26}$—, —$(CH_2)_xOC(O)NR^{26}$—, —$(CH_2)_xNR^{26}C(O)O$—, —$(CH_2)_xNR^{26}C(O)$—, —$(CH_2)_xC(O)NR^{26}$— or —$(CH_2)_xNR^{26}C(O)$— then $R^{26}$ is preferably hydrogen, methyl or ethyl, more preferably hydrogen.

In the compounds of formula (XIV) preferably the vinyl group is para to the group —$K^3$—$B^8$—$Q^4$.

Preferably $B^9$ is:

an alkylene group of formula —$(CR^{29}_2)_y$—, wherein the groups —$(CR^{29}_2)$— are the same or different, and in each group —$(CR^{29}_2)$— the groups $R^{29}$ are the same or different and each group $R^{29}$ is hydrogen or $C_{1-4}$ alkyl, preferably hydrogen, and y is from 1 to 12, preferably 1 to 6;

an oxaalkylene group such as alkoxyalkyl having 1 to 6 carbon atoms in each alkyl moiety; or an oligo-oxaalkylene group of formula —$[(CR^{30}_2)_{yy}O]_{xx}(CR^{30}_2)_{yy}$— where the groups —$(CR^{30}_2)$— are the same or different and in each group —$(CR^{30}_2)$— the groups $R^{30}$ are the same or different and each group $R^{30}$ is hydrogen or $C_{1-4}$ alkyl, preferably hydrogen, and yy is from 1 to 6, preferably 2 or 3, and xx is from 1 to 12, preferably 1 to 6.

Preferred groups $B^9$ include alkylene, oxaalkylene and oligo-oxaalkylene groups of up to 12 carbon atoms.

Particular examples of the group $B^9$ are —$CH_2$—, —$CH_2CH_2$— and —$(CH_2)_6$—.

The group $Q^5$ may be either anionic or cationic. Where the group $Q^5$ is anionic it may for example be a carboxylate, sulphonate, hydrogenphosphate or phosphate group. Where the group $Q^5$ is cationic it may for example be a group —$N.R^{31}_3$ in which each group $R^{31}$ is the same or different, and is hydrogen or alkyl of 1 to 6 carbon atoms two of which groups $R^{31}$ may together from a heterocyclic ring containing from 5 to 7 atoms, preferably hydrogen or methyl, a group N.Het, where Het is an unsaturated heterocyclic group such as pyridyl, substituted or unsubstituted by one or more alkyl groups of 1 to 4 carbon atoms, or a group —$P.R^{32}_3$ in which each group $R^{32}$ is the same or different and is hydrogen or alkyl of 1 to 6 carbons atoms, two of which groups $R^{31}$ may together form a heterocyclic ring containing from 5 to 7 atoms, preferably methyl.

Particular examples of comonomers bearing an ionic group include acrylic acid, methacrylic acid, 2-sulfoethyl methacrylate, 2-methacryloyloxyethyl phosphate, p-styrene sulfonic acid, 2-(methacryloyloxyethyl) trimethylammonium chloride, 3-aminopropyl methacrylamide and vinylbenzyl trimethylammonium chloride.

Comonomers containing an ionic group such as those of formula (XIII) and (XIV) are commercially available or may be prepared by conventional techniques using known reactions.

A.3. Diluent Comonomers

In addition to A.1. the residues of monomers containing a zwitterionic, and optionally A.2. residues of comonomers containing an alkyl (optionally substituted) hydrophobic group, reactive functional group or ionic group, the polymers (A) bearing pendant zwitterionic groups may comprise residues of a diluent comonomer.

Such diluent comonomers may be used to give the polymer physical and mechanical properties desirable for blending with the polymer (B) for example to improve miscibility. They may be of any known conventional radical polymerisable, preferably ethylenically unsaturated, type compatible with other comonomer(s).

Particular examples of diluent comonomers include alkyl (alk)acrylate preferably containing 1 to 4 carbon atoms in the alkyl group of the ester moiety, such as methyl (alk) acrylate; a mono- or, usually di-alkylamino alkyl(alk)

acrylate, preferably containing 1 to 4 carbon atoms in the or each alkyl moiety of the amine and 1 to 4 carbon atoms in the alkylene chain, e.g. 2-(dimethylamino)ethyl (alk) acrylate; and (alk)acrylamide, such as acrylamide; an alkyl- or dialkyl- (alk)acrylamide preferably containing 1 to 4 carbon atoms in the alkyl group of the amide moiety; a hydroxyalkyl (alk)acrylate preferably containing from 1 to 4 carbon atoms in the hydroxyalkyl moiety, e.g. a 2-hydroxyethyl (alk)acrylate; a vinyl monomer such as an N-vinyl lactam, preferably containing from 5 to 7 atoms in the lactam ring, for instance vinyl pyrrolidone, or an ester such as vinyl acetate; or styrene or a styrene derivative which for example is substituted on the phenyl ring by one or more alkyl groups containing from 1 to 6, preferably 1 to 4, carbon atoms, and/or by one or more halogen, such as fluorine atoms, e.g. (pentafluorophenyl)styrene.

Other suitable diluent comonomers include polyhydroxyl, for example sugar, (alk)acrylates and (alk)acrylamides in which the alkyl group contains from 1 to 4 carbon atoms, e.g. sugar acrylates, -methacrylates, -ethacrylates, -acrylamides, -methacrylamides and -ethacrylamides. Suitable sugars include glucose and sorbitol. Particularly suitable diluent comonomers include methacryloyl glucose or sorbitol methacrylate.

Further diluents which may be mentioned specifically include polymerisable alkenes, preferably of 2–4 carbon atoms, eg. ethylene, dienes such as butadiene, alkylene anhydrides such as maleic anhydride and cyano-substituted alkylenes, such as acrylonitrile.

Diluent comonomers may be obtained by conventional known methods.

Of the above diluent comonomers some are inert and act simply to modify the physical and mechanical properties of copolymers containing them. Others, and in particular the hydroxyalkyl(alk)acrylates and polyhydroxyl (alk)acrylates have a reactive role in addition to simply modifying physical and mechanical properties. Such comonomers contain functional groups, such as hydroxyl groups, which may react with a crosslinking group or may react with reactive groups in other molecules to attach them to the copolymer.

Preparation of Polymer (A)

The polymers (A) bearing pendant zwitterionic groups formed from polymerisable ethylenically unsaturated groups may be prepared by conventional techniques for polymerisation, typically thermal or photochemical polymerisation. Where comonomers capable of producing crosslinking are present, the polymerisation conditions are set such that crosslinking does not occur during polymerisation. Thus, for example, actinic radiation would not be used to prepare a polymer containing a monomer which can form crosslinks by exposure to actinic radiation.

For thermal polymerisation a temperature from 40 to 100° C., typically 50 to 80° C. is used. For photochemical polymerisation actinic radiation such as gamma, U.V., visible, or microwave radiation may be used. Typically U.V. radiation of wavelength 200 to 400 nm is used.

The polymerisation is generally performed in a reaction medium, which is for instance a solution or dispersion using as a solvent for example acetonitrile, dimethyl formamide, chloroform, dichloromethane, ethyl acetate, dimethyl sulphoxide, dioxan, benzene, toluene, tetrahydrofuran, or where the polymer does not contain groups which react with protic solvents, water or an alkanol containing from 1 to 4 carbon atoms, e.g. methanol, ethanol or propan-2-ol. Alternatively, a mixture of any of the above solvents may be used.

The polymerisation may be carried out in the presence of one or more polymerisation initiators, usually free radical generators, usually peroxides or azo initiators, such as benzoyl peroxide, 2,2'-azo-bis(2-methylpropionitrile) or benzoin methyl ether. Other polymerisation initiators which may be used are disclosed in"Polymer Handbook", 3rd edition, Ed. J. Brandrup and E. H. Immergut, Pub. Wiley-Interscience, New York, 1989.

Generally the polymerisation is performed for 1 to 72 hours, preferably 8 to 48, for instance 16 to 24 hours, and under an inert atmosphere of for example nitrogen or argon. The polymer is generally purified by dialysis, precipitation in a non-solvent (e.g. diethyl ether or acetone) or ultrafiltration. The resulting polymer is generally dried under vacuum, eg. for 5 to 72 hours and has a molecular weight from 10,000 to 10 million, preferably from 20,000 to 1 million.

The precise proportion and nature of the various comonomers used to prepare a copolymer comprising residues of a comonomer containing a zwitterionic group and a further comonomer may be adjusted to provide a copolymer which is particularly suitable for blending to a particular polymer (B). The monomer composition which is subjected to polymerisation to provide a polymer according to the invention comprises a minimum of 0.01%, preferably 1%, more preferably 5% by weight of monomer or monomers containing a zwitterionic group bearing a centre of permanent positive charge and a maximum of 99.9%, preferably 99%, more preferably 95% by weight of other monomer or monomers. Such other monomer or monomers may be a monomer or monomers containing an optionally substituted alkyl (usually hydrophobic) group, a reactive functional group, an ionic group or a diluent monomer or monomers.

Where the polymer (A) is a copolymer comprising residues of comonomer bearing zwitterionic groups and comonomer containing an optionally substituted alkyl group then preferably the comonomer composition comprises no more than 95%, more preferably no more than 90% and even more preferably no more than 80% by weight of comonomer or comonomers containing an alkyl group (eg hydrophobic alkyl, fluoroalkyl or siloxane group) the balance of the composition being comonomer or comonomers containing a zwitterionic group diluent monomer or monomers and/or crosslinkable monomer or monomers (i.e. which cross-link during the polymerisation reaction). Such a composition typically comprises up to 50% by weight of diluent comonomer or comonomers. Where diluent comonomer is present, it preferably comprises at least 1%, more preferably 5%, by weight of the total comonomer composition. Where present, crosslinkable comonomer or comonomers generally comprise from 0.1% to 20% by weight of the total comonomer composition.

Preferably the molar ratio such a copolymer of comonomer residues bearing a zwitterionic group to comonomer residues containing a hydrophobic alkyl, fluoroalkyl or siloxane group is from 5:95 to 80:20, more preferably 10:90 to 50:50. In addition the copolymer preferably comprises from 5% to 50%, more preferably 10% to 25%, by mole residues of diluent monomer and/or from 0.1 to 20%, more preferably 1% to 10%, by mole residues of crosslinkable comonomer, provided that where residues of both diluent and crosslinkable comonomer are present, they do not exceed in combination 50%, preferably 35% by mole.

Where the polymer (A) is a copolymer comprising residues of a comonomer which comprises a reactive group or ionic group, preferably the molar ratio of residues of bearing a zwitterionic group to residues containing a reactive group or ionic group is from 10:90 to 95:5, more preferably 50:50 to 90:10. In addition the copolymer preferably comprises from 5% to 50%, more preferably 10% to 25%, by mole residues of diluent monomer and/or from 0.1 to 20%, more preferably 1% to 10%, by mole residues of crosslinkable comonomer, provided that where residues of both diluent and crosslinkable comonomer are present, they do not exceed in combination 50%, preferably 35% by mole.

In addition the monomer or comonomer composition may comprise further components such as a polymerisation initiator, chain transfer agent, acid, base, surfactant, emulsifier or catalyst of conventional type each in an amount from 0.1% to 5%, typically from 0.2% to 3% and preferably about 0.5%, by weight each relative to the total weight of the monomers.

(B) Polymers Having Desirable Physical and/or Mechanical Properties

According to the present invention, the polymer (A) containing pendant zwitterionic groups is blended with a polymer (B) having desirable physical and/or mechanical properties. Such a polymer may be a thermoplastic, elastomer or thermosetting material. Preferably, the polymer (B) is a thermoplastic such as a polyolefin, polyvinylchloride (PVC), poly(alk)acrylate, such as methyl methacrylate, polyurethane, or fluorinated polyolefin.

In particular, the polymer (B) may be a polymer or copolymer, or a mixture of polymers or copolymers, which is already known for use in a particular application, such as a biomedical application. Table 1 below lists known polymers with biomedical applications which may be used in the blends of the present invention:

TABLE 1

| POLYMER | USES |
| --- | --- |
| Acrylate elastomers. | Prostheses |
| Chlorosulfonated polyethylene (Hypalon). | Vascular surfaces |
| Pure natural rubber. | |
| Polyurethanes (Esthane) (Ostamer) (Biomer) (Pellethane) (Lycra/ Spandex) (Cardiothane) (Tecoflex). | Prostheses, artificial hearts, vascular surfaces. |
| Silicone rubber (Silastic). | Artificial hearts and valves, blood oxygenator films, shunts. |
| Cellophane. | Dialysis membranes. |
| Cellulose acetate. | |
| Fluorocarbons (Teflon) (PVDC) (FEP) (PVOF) | Vascular and bulk implants. |
| Polysulfones | Separation Membranes. |
| Polyhydroxyethylmethacrylate (PHEMA). | Contact lenses, drug deliver, catheters, |
| Polymethylmethacrylate (PMMA) (Lucite) (Plexiglas) (Perspex). | suture coatings, prostheses, wound care dressings. |
| Polyethylmethacrylate (PEMA). | |
| Polyamides (Nylon) (Dacron). | Sutures, fabrics. |
| Polyethyleneterephthalate (Terylene) (Mylar). | |
| Silk. | |
| Polymonochloro-p-xylene. | Encapsulants of |
| Epoxy resins. | electronic components for implantation. |
| Polyethylene (Vitrathene). | Prostheses, tubing. |
| Polypropylene. | Components of blood |
| Polycarbonates | oxygenators and |
| Polystyrene | dialyzers, heart valves. |
| Polyvinylalcohol. | Dialysis films. |
| Polyvinylchloride (PVC). | Blood bags, blood |
| Vinylchloride copolymers | tubing, prostheses. |
| Polyvinylidenechoride. | Vascular surfaces. |

Generally the blends of the present invention will contain from 1 to 90% by weight of polymer (A) containing pendant zwitterionic groups and from 99 to 10% of polymer (B) having desirable physical and/or mechanical properties. The precise proportions of the polymers (A) and (B) will depend upon the compatibility of the two polymers for blending and, it may be necessary to test the polymers together for their compatibility. This may be achieved by blending different proportions of the polymers (A) and (B) to obtain a blend with the desired balance of mechanical and physical properties as well as biocompatibility. In particular, the proportions of the two polymers may be adjusted so as to obtain desired impact resistance, tensile strength, flexural modulus, low temperature brittleness, friction co-efficient, film permeability, film tear resistance, film shrinkage, surface and volume resistivity, surface wettability and/or contact angle.

The minimum quantity of polymer (A) will depend upon the particular polymer (B), the content of zwitterionic groups in the polymer (A) and the desired use of the blend. However, the content of polymer (A) should be sufficient to provide a detectable modification to the biocompatible properties of the blend compared to the unblended polymer (B). Preferably the blend will contain at least 1%, more preferably 10% and still more preferably 30% of polymer (A). The improvement in each of the fibrinogen absorption and the platelet activation should be so as to achieve a value of less than 80%, more preferably less than 60% of the value of polymer B alone.

It is believed the improved biocompatibility is due in part to increased hydrophilicity compared to the base polymer. Another property which improves and which may also be due in part to increased hydrophilicity is lubricity i.e. a reduced co-efficient of friction. The improved wettability due to increased hydrophilicity (which can be observed by determining the contact angle of water on the surface) may allow water to act as a wetting lubricant to a greater extent due to the zwitterionic groups. This may be a desirable property, for instance where a product is required to slide easily in contact with other surfaces, eg within the body, minimal modification to the biocompatible properties may be tolerated in the invention if accompanied by increased lubricity especially where a product is in contact with the body for a short time only, eg catheters and the like.

This increased lubricity forms the basis for a further invention in which the coefficient of friction in the presence of aqueous liquid of the surface of an article is reduced by the provision of bound zwitterionic groups.

In this invention the zwitterionic groups may be any of those defined by group X above. The zwitterionic group, is bound at the surface such that it is not removed by aqueous liquid in contact with the surface and so is usually covalently bound to polymer which forms the surface or is on the surface and which is water-insoluble. In some circumstances it may be possible for the zwitterionic group to be a part of a polymer which is itself water-soluble but is bound to a substrate surface so that it cannot be removed by water e.g. by being bound by strong ionic bonds or by hydrogen-bonding interaction.

In the preferred embodiment of the invention the zwitterionic groups are introduced at the surface of the article as pendant groups on a polymer A which is blended with a polymer B having suitable physical and/or mechanical properties and the blend of the polymers is then used to form the article, for instance by shaping as described above. However it is alternatively possible to introduce the zwitterrionic groups by coating a polymer containing such groups on to the surface of a preformed article. The polymer may, after coating, be bound to the article by hydrogen-bonding interactions, by chemical reaction to provide a covalent bond with the underlying polymer surface or by counterionic attraction between oppositely charged ionic groups on the coating polymer and on the coated surface. Products of this type are described in our earlier application (not published at the priority date of the first invention herein) WO-A-9301221.

Other ways of providing articles having zwitterionic groups at the surface where the article is formed of a reactive, usually polymeric material are by chemical reaction of a preformed article with a reagent which comprises the zwitterionic group and a chemically reactive group which is suitable for reaction with the material at the surface. Various derivatisation reactions of this type are described in our earlier applications EP-A-0032622, EP-A-0157469, WO-A-9113639 and WO-A-9305081. A further way of incorporating the zwitterionic group is to form a polmer from monomers including at least one monomer which has a zwitterionic group. Such monomers may be for formation of polyesters, for instance as described in our earlier publication EP-A-0275293, for formation of polyurethanes, for instance as described in EP-A-0199790, or for formation of addition polymers from ethylenically unsaturated monomers for instance as described in WO-A-9207885.

The utility of this invention is primarily in the medical field,for instance for any instrument which is. required to slide against any other surface in the presence of aqueous liquid, usually body fluids. Such instruments are for instance catheters, guide wires, endoscopes, instruments used in keyhole surgery, ostomy connectors or other permanent ports, dilators of various types, contact lenses, etc. The increased lubricity can be demonstrated qualitatively by observing the slipperiness of the article in the presence of water or other aqueous liquid. The coefficient of friction measured by routine techniques can be used to give a quantitative measurement of the increased lubricity, for instance as compared to the article formed in the absence of the zwitterionic groups or polymer containing the zwitterionic groups.

In addition, the blends of the present invention may further comprise conventional additives used in polymeric materials such as plasticisers, fillers, colourants, UV absorbers, anti-oxidants and/or preservatives, such as biocides, which may be included in conventional amounts so as to be compatible with the polymers present in the blend.

The present invention further provides a process for producing a blend of the present invention, which comprises blending a preformed polymer (A) bearing zwitterionic pendant groups and a polymer (B) having desirable mechanical and/or physical properties.

Such blending may be carried out by conventional techniques for blending solid or liquid polymeric materials, including known solid state physical mixing techniques such as roll-milling, Banbury mixing, screw extrusion and disk compounding. Alternatively, blending may be carried out using aqueous dispersions and/or solutions of the polymers (A) and (B) or dispersions and/or solutions of the polymers (A) and (B) in an organic solvent and the water and/or solvent removed for instance by evaporation or by precipitation of polymer followed by liquid/solid separation as normal. Such blending may be carried out using conventional liquid phase blending techniques such as high or low shear mixers. These techniques are used as for known polymer blending operations. Using routine procedures suitable mixing conditions and choice of ingredients can be selected to obtain a blend having the desired homogeneity. Crosslinking or other chemical reacion may take place during mixing, as is known in the blending art.

Where the polymer (B) is a thermoset polymer, blending by such mixing techniques may not be possible. In such circumstances, it may therefore be necessary to include the polymer (A) in a blend with the monomers of the polymer (B) or a pre-polymer of polymer (B) prior to final polymer formation eg cross-linking to form the thermoset material. Clearly, in such circumstances, polymer (A) must be able to withstand the polymerisation conditions and/or cross-linking conditions for polymer (B) without adverse effects. Where the polymer (A) also includes reactive or cross-linkable groups, then these may take part in the thermosetting reaction or crosslink to the polymer (B) to modify the properties of the final blended polymer.

The invention further provides a shaped article formed from a polymeric blend according to the present invention. Such articles may be formed in a conventional manner, for example by extrusion or injection moulding or other moulding techniques and/or by machining as necessary for the desired end shape appropriate to the nature of the particular material in question, for instance for the uses mentioned in table 1 above, in which the surface of the article is in contact with a biological liquid. Usually a protein- or cell-containing liquid, such as blood, plasma, serum or tear film.

In particular, the blends of the present invention are suitable for use in surgical implants or prostheses, bioseparation apparatus, blood carrier bags, dialysis membranes, blood oxygenator films, tubing for use in prostheses, in extra corporeal circuitry or in catheters, connectors, stoppers, closures for diagnostic catheters, surgical drapes and tapes, and encapsulants for bio-medical applications. In addition, they are suitable for use as casings for electronic devices, as contact lenses, intra-ocular lenses and other ophthalmic implants and cell culture materials.

The blends of the present invention are preferred to graft polymers with zwitterionic groups formed according to WO-A-9305081 as they allow for a wider range of base polymers A and B to be used and, since the polymers can be purified to remove unreacted monomer or low molecular weight oligomer before blending with ease, provide products without problems of contamination by low molecular weight impurities.

The present invention will now be illustrated by the following Examples:

EXAMPLES

The following assays have been used to evaluate the blends according to the present invention:
Water Content
  A sample of the blend is soaked in deionised water, removed when equilibrium is reached, excess surface water is removed, the sample is weighed, dried under vacuum until there is no further weight change (eg at a raised temperature in the range 60 to 120° C. as appropriate) and reweighed.
Protein Adsorption Using an Enzyme Immunoassay
  The assay determines absorption of human fibrinogen, a components of blood serum, at a surface. This protein is representative of protein which is typically adsorbed at a surface in contact with blood. The assay can be readily modified to determine the absorption of other proteins.
  Discs (7 mm in diameter) of untreated material (as controls) and material treated with polymer as described below, were prepared and washed with phosphate buffered saline (PBS) for at least 10 minutes in the wells of microplates. The samples were incubated with human plasma (300

μl) for 10 minutes and then washed with PBS three times. Each of the test samples and each of the control samples were treated with human fibrinogen-specific antibody (300 μl) for 30 minutes and again washed with PBS three times. As a control for non-specific binding of antibody to the samples, each sample was also incubated with non-specific antibody (300 μl) for 30 minutes. A conjugate of horseradish peroxidase and a second antibody specific to the first antibody (300 μl) was added to both the test samples and the controls and incubated for 30 minutes before washing. Each of the test samples and the controls were transferred to new microplates and a solution of 2,2'-azino-bis(3-ethyl benzthiazoline-6-sulphonic acid) (ABTS) in phosphate-citrate buffer (300 μl, 0.6 mg/ml) added, the reaction was allowed to proceed for 10 minutes. At this time an aliquot of the mixture (200 μl) was removed and added to a solution of citric acid and sodium azide in distilled water (20 μl, 0.21 g/ml and 2 mg/ml respectively). The optical density of the solutions was measured using a Techgen automated plate reader at 650 nm using the ABTS solution as blank.

In an alternative procedure, rather than using ABTS, each of the samples was transferred to wells of new microplates and a solution of o-phenylene diamine (OPD) in phosphate-citrate buffer (300 μl, 0.4 mg/ml) added, and the reaction was allowed to proceed for 10 minutes. At this time an aliquot of the mixture (200 μl) was removed from each well and the optical density of the solutions was measured using a Techgen automated plate reader at 450 nm using the OPD solution as blank.

Activated Platelet Study

Blood was collected from a healthy adult volunteer using the double syringe method where the first 5 ml of blood is discarded. The blood was collected into tri-sodium citrate (32 g/l) in the proportion of 9 volumes to 1 volume citrate in plastic tubes. The samples were kept at room temperature on a spiral mixer until used.

Discs (7 mm in diameter) of untreated material as controls and material treated with polymers as described below were prepared and placed into the wells of a microplate. The samples were incubated with whole fresh citrated blood (200 μl) on a rotary mixer for 30 minutes before washing in PBS four times. Platelet activation was measured by a proprietary assay [Lindon, J. N. et al., *Blood*, 68, 355 (1986)].

In an alternative procedure half of the test replicates were incubated with citrated blood (200 μl) and the remainder were incubated with EDTA-treated blood on a phase shaker for 30 minutes before washing in PBS four times. Platelet activation was measured in a manner similar to that described above for detection of proteins by enzyme immunoassay using antibodies against GMP140 to detect the presence of this platelet activation marker on the surface of biomaterials. In the presence of EDTA, which extracts calcium from inside platelets, activation is inhibited, so that incubation with EDTA-treated blood acts as a non-specific control for activation, obviating the need for incubation in non-specific antibody.

Example 1

Preparation of Poly(2(methacryloyloxyethyl)-2'-(trimethylammonium)ethyl Phosphate Inner salt-co-n-dodecyl Methacrylate (1:2)/High Density Polyethylene Blend High density polyethylene resin (35 g, 0.964 g/cm, Mw=125,000, Mn=18,000), was formed into a hide on a two roll mill at 150° C. Poly(2(methacryloyloxyethyl)-2'-(trimethylammonium)ethyl phosphate inner salt-co-n-dodecyl methacrylate (1:2) (15 g) was added and the mixture blended for 10 minutes. The hide was then removed, cooled to room temperature, cut into pieces and pressed into a film (under a pressure of 10 ton/ft$^2$, at 145° C., for 10 min.) between polyethyleneteraphthalate backing sheets. The film was tested for its protein adsorption and platelet activation properties. The results are in table 2 below.

Example 2

Preparation of Poly(2(methacryloyloxyethyl)-2-(trimethylammonium)ethyl Phosphate Inner salt-co-n-octadecyl Methacrylate (1:2)/High Density Polyethylene Blend High density polyethylene resin (35 g, 0.964 g/cm, Mw=125,000, Mn=18,000), was formed into a hide on a two roll mill at 150° C. Poly(2(methacryloyloxyethyl)-2'-(trimethylammonium)ethyl phosphate inner salt-co-n-octadecyl methacrylate (1:2) (15 g) was added and the mixture blended for 10 minutes. The hide was then removed, cooled to room temperature, cut into pieces and pressed into a film (10 ton/ft$^2$, 145° C., 10 min.) between polyethyleneterephthalate backing sheets. into a film (10 ton/ft$^2$, 145° C., 10 min.) between polyethyleneterephthalate backing sheets.

Example 3

Preparation of Poly(2(methacryloyloxyethyl)-2'-(trimethylammonium)ethyl Phosphate Inner Salt-co-n-dodecyl Methacrylate (1:2)/Low Density Polyethylene Blend Low density polyethylene resin (35 g, 0.920 g/cm), was formed into a hide on a two roll mill at 150° C. Poly(2-(methacryloyloxyethyl)-2'-(trimethylammonium)ethyl phosphate inner salt-co-n-dodecyl methacrylate (1:2) (15 g) was added and the mixture blended for 10 minutes. The hide was then removed, cooled to room temperature, cut into pieces and pressed into a film (10 ton/ft$^2$, 145° C., 10 min.) between polyethyleneteraphthalate backing sheets. The film was subjected to protein deposition and platelet activation tests and the results are in table 2.

TABLE 2

| ASSAY RESULTS AND CONTROL % reduction vs. (control) normalised to 100% | | |
|---|---|---|
| Example No. | Protein Adsorption | Platelet Activation |
| 1 | 59 (non-blended HDPE) | 37 (non-blended HDPE) |
| 2 | 49 (non-blended LDPE) | 52 (non-blended LDPE) |

Example 4

Preparation of Poly(2(methacryloyloxyethyl)-2'-(trimethylammonium)ethyl Phosphate Inner Salt-co-n-octadecyl Methacrylate (1:2)/Low Density Polyethylene Blend Low density polyethylene resin (30 g, 0.920 g/cm), was formed into a hide on a two roll mill at 150° C. Poly(2(methacryloyloxyethyl)-2'-(trimethylammonium)ethyl phosphate inner salt-co-n-octadecyl methacrylate (1:2) (20 g) was added and the mixture blended for 10 minutes. The hide was then removed, cooled to room temperature, cut into pieces and pressed into a film (10 ton/ft$^2$, 145° C., 10 min.) between polyethyleneteraphthalate backing sheets.

Example 5

Preparation of Poly(methacryloyloxyethyl)-2'-(trimethylammonium)ethyl Phosphate Inner Salt/Natural Rubber Latex Blend Reference Example 1

Poly(methacryloyloxyethyl)-2'-(trimethylammonium) ethyl phosphate inner salt (2.00 g) was dissolved in water (6.00 g) and to this solution natural rubber latex (6.00 g, 37% solids) was added with stirring. A small amount of coagulated material (0.10 g dry weight) was generated and removed. The mixture was then cast on to a glass plate in a well formed by a sheet of PTFE with the centre removed, clamped to the glass with bulldog clips. The cast film was then cured in an oven at 140° C. for 20 minutes to remove water by evaporation. The pale brown transparent sheet was then allowed to cool to room temperature then washed (readily wetting) repeatedly with water to give a cream coloured opaque sheet. The sheet had a high degree of self tackiness and readily stuck to itself irreversibly. The sheet had a water content of (22%).

Example 6

Preparation of Poly(methacryloyloxyethyl)-2'-(trimethylammonium)ethyl Phosphate Inner salt-co-methacryloyloxyethyltrimethylammonium Bromide (7:3)/Natural Rubber Latex Blend Poly(methacryloyloxyethyl)-2'-(trimethylammonium) ethyl phosphate inner salt-co-2-methacryloyloxyethyltrimethylammonium bromide (7:3) (2.5 g) was dissolved in water (7.20 g) and filtered through glass wool to give 6.70 g of solution. To this solution natural rubber latex (6.00 g, 37% solids) was added with stirring. A small amount of coagulated material (0.24 g dry weight) was generated and removed. The mixture was then cast on to a glass plate in a well, formed by a sheet of PTFE with the centre removed, clamped to the glass with bulldog clips. the cast film was then cured in an oven at 140° C. for 20 minutes. The pale brown transparent sheet was then allowed to cool to room temperature then washed (readily wetting) repeatedly with water to give a highly swollen cream coloured opaque sheet. The sheet was non tacky and highly lubricious to the touch. The sheet had a water content of 86% and showed a reduction in fibrinogen adsorption, relative to the control cast natural rubber latex sheet of 51%.

Example 7

Preparation of Poly(methacryloyloxyethyl)-2'-(trimethylammonium)ethyl Phosphate Inner salt-co-3-chloro-2-hydroxyropylmethacrylate (4:1)/Natural Rubber Latex Blend Poly (methacryloyloxyethyl)-2'-(trimethylammonium) ethyl phosphate inner salt-co-3-chloro-2-hydroxypropylmethacrylate (4:1) (2.00 g) and sodium hydroxide (0.1178 g) were dissolved in water (6.00 g), and to this solution natural rubber latex (6.00 g, 37% solids) was added with stirring. The mixture was then cast on to a glass plate in a well, formed by a sheet of PTFE with the centre removed, clamped to the glass with bulldog clips. The cast film was then cured in an oven at 140° C. for 20 minutes. The pale brown transparent sheet was then allowed to cool to room temperature then washed (readily wetting) repeatedly with water to give a cream coloured opaque sheet. The sheet was non tacky and lubricious to the touch. The sheet had a water content of 39%.

Example 8

Preparation of Poly(methacryloyloxyethyl-2'-(trimethylammonium)ethyl Phosphate Inner Salt/Natural Rubber Latex Blend Poly(methacryloyloxyethyl)-2'-(trimethylammonium) ethyl phosphate inner salt (2.00 g) was dissolved in water (6.00 g) and to this solution natural rubber latex (6.00 g, 37% solids) was added with stirring. A small amount of coagulated material (0.10 g dry weight) was generated and removed. The mixture was then cast on to a glass plate in a well, formed by a sheet of PTFE with the centre removed, clamped to the glass with bulldog clips. The cast film was then cured in an oven at 140° C. for 20 minutes. The pale brown transparent sheet was then allowed to cool to room temperature then washed (readily wetting) repeatedly with water to give a cream coloured opaque sheet. The sheet had a high degree of self tackiness and readily stuck to itself irreversibly.

Example 9

Preparation of Poly(methacryloyloxyethyl-2'-(trimethylammonium)ethyl Phosphate Inner Salt-co-dodecylmethacrylate (1:21)/Methacrylate Blend Poly(methacryloyloxyethyl)-2'-(trimethylammonium) ethyl phosphate inner salt-co-dodecylmethacrylate (1:2) (3.00 g), methylmethacrylate (7.00 g), dichloromethane (40.0 g) and methanol (1.0 g) were mixed to give a dispersion. This mixture was cast on to a glass plate using two 0.5 mm thick steel spacers and a steel spreading blade. The cast film was allowed to dry in air for 16 hours then stored in water. The sheet had a water content of 16% and showed a reduction in fibrinogen adsorption, relative to the control cast sheet of the methylmethacrylate of 41%.

Example 10

Preparation of Poly(methacryloyloxyethyl-2'-(trimethylammonium)ethyl Phosphate Inner Salt-co-dodecylmethacrylate (1:2)/Polycarbonate Blend Poly(methacryloyloxyethyl)-2'-(trimethylammonium) ethyl phosphate inner salt-co-dodecylmethacrylate (1:2) (3.00 g), polycarbonate 7.00 g), dichloromethane (40.0 g) and methanol (1.0 g) were mixed to give a,.dispersion. This mixture was cast on to a glass plate using two 0.5 mm thick steel spacers and a steel spreading blade. The cast film was allowed to dry in air for 16 hours then stored in water. The sheet had a water content of 13%.

Example 11

Preparation of Poly(methacryloyloxyethyl-2'-(trimethylammonium)ethyl Phosphate Inner salt-co-dodecylmethacrylate (1:2)/Polystyrene Blend Poly(methacryloyloxyethyl)-2'-(trimethylammonium) ethyl phosphate inner salt-co-dodecylmethacylate (1:2) (3.00 g), polystyrene (7.00 g), dichloromethane (40.0 g) and methanol (1.0 g) were mixed to give a dispersion. This mixture was cast on to a glass plate using two 0.5 mm thick steel spacers and a steel spreading blade. The cast film was allowed to dry in air for 16 hours then stored in water. The sheet had a water content of 10% and showed a reduction of fibrinogen adsorption, relative to the control cast sheet of the polystyrene of 28%.

Example 12

Preparation of Poly(methacryloyloxyethyl-2'-(trimethylammonium)ethyl Phosphate Inner salt-co-dodecylmethacrylate (1:2)/Polysulfone Blend Poly (methacryloyloxyethyl)-2'-(trimethylammonium) ethyl phosphate inner salt-co-dodecylmethacylate (1:2) (3.00 g) polysulfone (7.00 g), dichloromethane (40.0 g) and methanol (1.0 g) were mixed to give a dispersion. This mixture was cast on to a glass plate using two 0.5 mm thick steel spacers and a steel spreading blade. The cast film was allowed to dry in air for 16 hours then stored in water. The sheet had a water content of 11%.

Example 13

Preparation of Poly(methacryloyloxyethyl-2'-(trimethylammonium)ethyl Phosphate Inner salt-co-dodecylmethacrylate (1:2)/Methylmethacrylate Blend Poly(methacryloyloxyethyl)-2'-(trimethylammonium) ethyl phosphate inner salt-co-dodecylmethacylate (1:2) (5.00 g), methylmethacrylate (5.00 g), dichloromethane (40.0 g) and methanol (1.0 g) were mixed to give a dispersion. This mixture was cast on to a glass plate using two 0.5 mm thick steel spacers and a steel spreading blade. The cast film was allowed to dry in air for 16 hours then stored in water. The sheet had a water content of 26% and showed a reduction in fibrinogen adsorption, relative to the control cast sheet of methylmethacrylate of 48%.

Example 14

Preparation of Poly(methacryloyloxyethyl-2'-(trimethylammonium)ethyl Phosphate Inner salt-co-n-butylmethacrylate (1:2)/Methylmethacrylate Blend Poly(methacryloyloxyethyl)-2'-(trimethylammonium)-ethyl phosphate inner salt-co-n-butylmethacrylate (1:2) (3.62 g), methylmethacrylate (6.38 g), dichloromethane (40.0 g) and methanol (1.0 g) were mixed to give a dispersion. This mixture was cast on to a glass plate using two 0.5 mm thick steel spacers and a steel spreading blade. The cast film was allowed to dry in air for 16 hours then stored in water. The sheet had a water content of 19% and showed a reduction in fibrinogen adsorption, relative to the control cast sheet of methylmethacrylate of 64%.

Example 15

Preparation of Poly(methacryloyloxyethyl-2'-(trimethylammonium)ethyl Phosphate Inner Salt-co-dodecylmethacrylate-co-1H,1H,2H,2H-heptadecafluorodecylmethacrylate (1:1:1)/Methylmethacrylate Blend Poly(methacryloyloxyethyl)-2'-(trimethylammonium) ethyl phosphate inner salt-co-dodecylmethacrylate-co-1H, 1H,2H,2-heptadecafluorodecylmethacrylate (1:1:1) (2.00 g), methylmethacrylate (8.00 g), dichloromethane (40.0 g) and methanol (1.0 g) were mixed to give a dispersion. This mixture was cast on to a glass plate using two 0.5 mm thick steel spacers and a steel spreading blade. The cast film was allowed to dry in air for 16 hours then stored in water. The sheet had a water content of 7%.

Example 16

70:30 Solution Blend of Polyacrylonitrile (PAN)/Polyvinylchloride (PVC) Copolymer and Poly(methacryloyloxyethyl)-2'-(trimethylammonium) ethyl Phosphate Inner Salt-co-alkyl Methacrylate Copolymers PAN/PVC (42 g) was mixed with the poly(methacryloyloxyethyl)-2'-(trimethylammonium)ethyl phosphate inner salt copolymer (including the comonomer mentioned in the table) (18 g) and dissolved in pyrrolidinone (660 g) at 60° C. A pale yellow solution formed which remained clear at room temperature. Blended polymer was isolated by dropwise addition to water (7 L) to give a precipitate. The precipitated polymer was washed with water (28 L) and dried in vacuo at 60° C. The results are given in Table 3.

TABLE 3

| | COPOLYMER | | | | | | |
|---|---|---|---|---|---|---|---|
| | | Ratio of Alkyl Methacrylate: methacryloyloxyethyl)-2'-(trimethylammonium) | | ELEMENTAL ANALYSIS FOUND (Theoretical) | | | |
| | Alkyl | | Yield | | | | |
| Example | Methacrylate | ethyl phosphate inner salt | (%) | C | H | N | P |
| 16.1 | Dodecyl | 2:1 | 96 | 53.5 (55.4) | 6.6 (6.7) | 7.7 (8.8) | 1.1 (1.1) |
| 16.2 | Octadecyl | 2:1 | 98 | 54.2 (56.5) | 6.7 (6.9) | 7.7 (8.7) | 0.93 (0.96) |
| 16.3 | Octadecyl | 1:2 | 97 | 50.9 (53.2) | 6.2 (6.4) | 8.1 (9.2) | 1.8 (2.0) |

Example 17

Formation of an Ultafiltration Membrane from a Solution Blend of PAN/PVC Copolymer and Poly(methacryloyloxyethyl)-2'-(trimethylammonium) ethyl Phosphate Inner salt-co-alkyl Methacrylates Blended materials from example 16 above were dissolved in pyrrolidinone to form solutions of between 10 and 20% weight volume., Membranes were cast on to clean glass plates at a thickness of between 100 and 200 µg (typically (150 µm). The solvent was allowed to evaporate for between 30 s and 5 minutes at a relative humidity of 50% and then the membrane was immersed in a water bath. Asymmetric ultrafiltration membranes formed with nominal cut-off of between 500 and 1,000,000 Daltons. The membranes had physical properties analogous to the non-blended materials. There was no measurable protein adsorption on the blended materials whereas the PAN/PVC showed considerable protein adsorption.

Example 18

Preparation of Poly(2(methacyloyloxyethyl)-2'-(trimethylammonium)ethyl Phosphate Inner Salt-co-n-dodecyl Methacrylate (1:2)/Polyurethane (Tecoflex) Blend Tecoflex (20 g), poly(2(methacryloyloxyethyl)-2'-(trimethylammonium)ethyl phosphate inner salt-co-n-dodecyl methacrylate (1:2) (1.1 g), ethyl acetate (40 g) and propan-2-ol (40 g) were mixed to give a solution, then the solvents removed on a rotary evaporator. The dry blended material was then pressed into a film (10 ton/ft$^2$, 110° C., 10 min.) between polyethylene terephthalate backing sheets.

Example 19

Preparation of Poly(2(methacyloyloxyethyl)-2'-(trimethylammonium)ethyl Phosphate Inner Salt-co-n-dodecyl Methacrylate (1:4)/Polyurethane (Tecoflex) Blend Tecoflex (7.5 g), poly(2(methacryloyloxyethyl)-2'-(trimethylammonium)ethyl phosphate inner salt-co-n-dodecyl methacrylate (1:4) (2.5 g), dichloromethan (100 g) were mixed to give a solution, then the solvents removed on a rotary evaporator. The dry blended material was then pressed into a film (10 ton/ft$^2$, 110° C., 10 min.) between polyethylene terephthalate backing sheets.

Reference Example 1

Preparation of 2(methacryloyloxyethyl)-2'-(trimethylammonium Ethyl Phosphate Inner Salt and Homopolymer Thereof The preparation is illustrated by the reaction scheme A which follows.

a) 2-Chloro-1,3-dioxaphospholane (1)

In a flask fitted with a pressure equalising dropping funnel, reflux condenser (fitted with a CaCl$_2$ guard tube) and magnetic stirrer, was placed a solution of phosphorus trichloride (220 ml; 346.3 g; 2.52 mol) in dichloromethane (500 ml). Ethylene glycol (139 ml; 154.7 g, 2.49 mol) was then added dropwise via the dropping funnel at such a rate that the evolution of HCl did not become too excessive. On the addition of the ethylene glycol, the condenser was arranged for distillation, and the dichloromethane removed at atmospheric pressure. When the distillate temperature reached 60° C. the flask was arranged for vacuum distillation using a water pump, Distillation then gave 2-chloro-1,3-dioxaphospholane (158 ml; 224.5 g; 71.3%) as a colourless mobile liquid (which fumes in moist air) b.pt. 36–40° C./21 mm Hg. [cf 45.5–47° C./20 mm Hg, Lucas et al, J. Am. Chem. Soc., 72, 5491, (1950)]. IR (cm$^{-1}$, thin film) 2980, 2905, 1470, 1210, 1005, 930, 813, 770.

b) 2-Chloro-2-oxo-1,3,2-dioxaphospholane (2)

In a flask fitted with a magnetic stirrer, reflux condenser (fitted with a CaCl$_2$ guard tube) and sintered glass gas inlet tube, was placed absolution of 2-chloro-1,3-2-dioxaphospholane (100.8 g; 0.797 mol) in dry benzene (200 ml). The solution was stirred and a steady stream of oxygen was bubbled through the solution. The reaction was mildly exothermic, and temperature control was achieved by allowing the solvent to ref lux. The oxygen was passed through the reaction mixture for 6 hours. The solvent was removed by rotary evaporation, and the colourless mobile residue distilled to give 2-chloro-2-oxo-1,3,2-dioxaphospholane (2) (87.41 g; 77%) as a colourless mobile liquid –b.pt 95–97° C./0.2 mbar [c.f. 102.5–105° C./1 mbar (Edmundson, Chem. Ind. (London)), 1828 (1962); 79° C./0.4 mbar (Umeda et al., Makromol. Chem. Rapid Commun., 3, 457, (1982)].

IR(cm$^{-1}$, thin film) 2990, 2910, 1475, 1370, 1310, 1220, 1030, 930, 865, 830.

c) 2(2-Oxo-1,3,2-dioxaphospholan-2-yloxy)ethyl methacrylate (3)

In a flask fitted with a magnetic stirrer, low temperature thermometer, and a pressure equalising funnel fitted with a silica gel guard tube, was placed a solution of 2-hydroxyethylmethacrylate (20.00 g, 0.154 mol) and triethylamine (15.60 g; 0.154 mol) in dry diethyl ether (300 ml). The solution was stirred and cooled to between –20° C. and –30° C. A solution of freshly distilled 2-chloro-2-oxo-1,3,2-dioxaphospholane(2) (21.9 g; 0.154 mol) in dry diethyl ether (20 ml) was then added dropwise over 30 minutes, the temperature being held at –20° C. during the addition. Stirring was continued at this temperature for a further 1 hour and then for a further hour as the reaction mixture was allowed to warm to room temperature. The precipitated triethylamine hydrochloride was removed by filtration, and was washed well with dry ether. The ether was removed from the combined filtrate and washings by rotary evaporation. The cloudy oil residue was then shaken for 5 minutes with dry diethyl ether (50 ml) to precipitate a further crop of triethylamine hydrochloride, which was again removed by filtration. Removal of the ether on the rotary evaporator gave (3) (34.18 g; 94.3%) as a colourless viscous oil.

IR (cm$^{-1}$, thin film) 1720, 1640, 1450, 1360, 1310, 1290, 1170, 1030, 930, 850. NMR (CDCl$_3$; 60 MHz, δ ppm) 1.95 (s,3H), 4.25–4.70 (m,8H), 5.70 (m,1H), 6.25 (m,1H). Rf 0.9 (SiO$_2$, eluting with 10% methanol: 90% dichloromethane; spot visualised with molybdenum blue spray reagent and with iodine vapour).

d) 2(Methaeryloyloxyethyl)-2'-(trimethylammonium)ethyl phosphate inner salt (4).

The phospholane (3) (67.20 g; 0.285 mol) was dissolved in 100 ml of dry acetonitrile, and placed in a heavy walled tissue culture bottle. The phospholane solution was then treated with a solution of anhydrous trimethylamine (25.74 g; 0.436 mol) in dry acetonitrile (100 ml). The vessel was then sealed, and placed in a water bath held at 50° C. for 30 hours. The vessel was opened, and the solution brought to the boil. The solution was filtered whilst hot, and then set aside for crystallisation.

The product was collected by filtration, and most of the solvent removed by suction. The wet product was then washed thoroughly with anhydrous ether, then dried under reduced pressure, to give (4) as a white amorphous, hygroscopic solid (51.16 g; 61%). Evaporation of the mother liquor gave a very viscous oil (20.00 g; 23%), from which further product (4) crystallised on standing at –20° C. TLC (silica gel plates, eluting with methanol/dichloromethane (1:1 v/v)) showed one spot Rf 0.1, which was revealed with Dragendorff's reagent, Molybdenum blue spray reagent, and iodine vapour.

IR(cm$^{-1}$ 1720, 1640, 1320, 1300, 1230, 1170, 970, 750. NMR (D$_2$O; 60 MHz; δ ppm) 2.0 (s,3H), 3.27 (s,9H) 3.60–4.50 (m, 8H), 5.80, (m,1H) and 6.25 (m,1H). CHN Found: C, 42.98%, H, 7.88%, N, 4.42%, P, 10.51%. CHN Theory: C, 44.75%, H, 7.46%, N, 4.75%, P, 10.51%.

Preparation of poly(methacryloyloxyethyl)-2'-(trimethylammonium)ethyl Phosphate Inner Salt (Methacryloyloxyethyl)-2'-(trimethylammonium)ethyl phosphate inner salt (20 g) was dissolved in propan-2-ol-(200 ml) and the solution purged with nitrogen (30 minutes). 2,2'-azo-bis(2-methylpropionitrile) (0.040 g) was added and the temperature raised to 60° C. The reaction solution was stirred under nitrogen for 40 hours then the solution allowed to cool to room temperature. The solvent was removed on a rotary evaporator and the solid redissolved in dichloromethane/methanol (80:20) solution (100 ml). The polymer was isolated by precipitation in acetone (1.5 L) followed by vacuum filtration under a nitrogen atmosphere. The product was then dried under vacuum at room temperature to give a yield of 18.2 g (91%).

NMR (200 MHz, d, ppm, $CD_3OD$)4.1–4.4(b),4.0–4.2(b), 3.6–3.8(b),3.3(s),1.8–2.2(b),1.0–1.6(b),1.0–1.2(b),0.8–1.1 (b) IR($cm^{-1}$, KBr disc) 3431, 2960, 1723, 1484, 1240, 117, 1088, 969, 792

Reference Example 2

Synthesis of Dimethyl(2-methacroyloxyethyl)-(1(2-sulphopropyl)) Ammonium Betaine Inner Salt 2(Dimethylamino)ethylmethacrylate was vacuum distilled and then dissolved in 0.1M dichloromethane. To this solution was added an equimolar amount of propane sultone. The betaine slowly precipitated out of solution and was recovered by filtration and washed with cold dichloromethane. The reaction is shown in Reaction Scheme B.

Reference Example 3

Preparation of 1[4(4'-vinylbenzyloxy)butane]-2"-(trimethylammonium)ethyl Phosphate Inner Salt.

The synthesis is depicted in Reaction Scheme C.
4-Hydroxy-1(4'-vinylbenzyloxy)butane (5)

Butanediol (40 ml; 40.68 g; 0.452 mol) was stirred in a 100 ml round bottomed flask, and treated portionwise with potassium butoxide (17.60 g; 0.144 mol). The initial reaction was exothermic. The reaction mixture was stirred for 1.5 hours at room temperature. The resulting cloudy solution was then treated with chloromethyl styrene (20.00 g; 0.131 mol). The styrene formed an upper, pale green layer, (the colouration being due to the presence of inhibitor), whose color darkened considerably on the addition of 18-crown-6 (0.49 g; 1.86×$10^{-3}$ mole). The flask was stoppered, protected from light, and stirred for 28 hours at room temperature. The mixture was then poured into water (120 ml) and extracted with dichloromethane (4×50 ml). The combined organic extracts were dried ($MgSO_4$) and evaporated to give viscous yellow oil (932.7 g). This oil was distilled from a small amount of CuCl to give a product showing some impurities on TLC. The oil was then chromatographed on silica gel, initially eluting with dichloromethane/petrol (1:1) to remove the impurities. The product was then eluted off the column with ethyl acetate/petrol (1:1). Evaporation of the solvent gave a colourless oil, which was distilled to give the desired styrylbutyl alcohol as a colourless oil b.pt. 150–152° C./0.4 mbar. Yield 18.70 g; 69.2%.

NMR (60 MHz: $CDCl_3$) 1.55 (m4H C—$CH_2$—C); 3.50 (m, 5H, 1H exch.; O—$CH_2$—, O—H), 4.45 (s,2H; Ar—$CH_2$—), 5.50 (dd, 2H, vinylic), 6.75 (dd, vinylic), 7.40 (m, 4H, Ar—H). IR 3402, 2938, 2888, 1631, 1602, 1582, 1511, 1480, 1445, 1382, 1320, 1116, 1063, 920, 907, 827, 801, 716 and 667 $cm^{-1}$ 4(2-Oxo-1,2,3-dioxaphospholane-2-yloxyl-1(4'-vinylbenzyloxy) butane (6)

4-Hydroxy-1(4'-vinylbenzyloxy)butane (5) (10.03 g; 48.69 mmol) and dried triethylamine (4.92 g, 48.69 mmol) were dissolved in dry diethyl ether (150 ml) and the resulting solution placed in a rigorously dried flask. The solution was cooled to −30° C. and 2-chloro-2-oxo-1,3,2-dioxaphospholane (6.94 g; 48.69 mmol) added dropwise over 30 minutes, the temperature being held at −30° C. The reaction mixture was then stirred for a further 2 hours, during which time the temperature was allowed to rise to 10° C. The mixture was filtered and the precipitate washed with dry ether. The filtrate was evaporated (20° C./21 mm) to give a cloudy oil. The residue was shaken with 50 ml of dry ether and refiltered. Evaporation of the filtrate gave the product as a viscous yellow oil (13.73 g; 90.4%).

TLC (eluting with 10% methanol 90% dichloromethane) showed one, major spot, which stained with acid molybdate reagent (Rf 0.61), IR (thin film) 3458, 2945, 2917, 2860, 1630, 1602, 1581, 1475, 1419, 1363, 1283, 1103, 1032, 820, 842, 807, 800, 715, 610 and 421 $cm^{-1}$.

1[4(4'-Vinylbenzyloxy)butane]-2"-(trimethylammonium) ethyl phosphate inner salt (7)

Trimethylamine (2.00 g, 33.9 mmol) was distilled into a reaction vessel, and frozen with liquid nitrogen. A solution of the 4(2-oxo-1,3,2-dioxaphospholane-2-yloxy)-1-(4'-vinylbenzyloxy)butane (6) (10.00 g, 32.1 mmol) in anhydrous acetonitrile (40 ml) was then added to the reaction vessel, which was then sealed and placed in a thermostatted water bath (50° C. for 50 hours). The reaction vessel was then cooled to room temperature, opened, and the reaction mixture evaporated to about half its original volume (21 mm pressure). The concentrated solution was then stirred at room temperature, whilst anhydrous ether (200 ml) was added dropwise to precipitate the product as a viscous oil. The mixture was then left for several hours at −10° C. The product was collected by decanting off the supernatant solid. TLC (eluting with methanol/dichloromethane 1:1) showed one major spot at Rf 0.0–0.1 which stained with both Dragendorffs reagent and acid molybdate.

Reference Example 4

Preparation of 2(acryloyloxyethyl-2'-(trimethylammonium)ethyl Phosphate Inner Salt The synthesis is essentially analogous to that described in Reference Example 1 and uses a synthetic strategy analogous to that shown in Reaction Scheme A.
(a) 2-(2-Oxo-1,3,2-dioxaphospholan-2-yloxy)ethyl acrylate
2-Hydroxyethyl acrylate (11.5 ml, 0.1M) and triethylamine (14.6 ml) in dry diethyl ether. (250 ml) were cooled to −25° C. under nitrogen as a solution of 2-chloro-2-oxo-1,3,2-dioxaphospholane (14.3 g) in dry diethyl ether was added over 20 minutes. The mixture was stirred for a further 1 hour at −20° C. and then allowed to warm to 10° C. over a further hour. The precipitate was filtered, washed with ethyl acetate (100 ml) and the combined filtrate and washings evaporated under reduced pressure to give a pale yellow oil (21 g).

$^1$H NMR (200 MHz) d ($CD_3CN$) 6.4 (1H,dd), 6.2 (1H, dd), 5.9 (1H,dd), 4.0–3.6 (8H, complex) ppm.
(b) 2-(Acryloyloxyethyl)-2'-(trimethylammonium)ethyl phosphate Inner Salt.

2-(2-Oxo-1,3,2-dioxaphospholan-2-yloxy) ethyl acrylate (21 g, 0.095M) in acetonitrile (50 ml) was treated with a solution of triethylamine (12.1 g) in acetonitrile (150 ml) in a pressure reactor at 50° C. for 17 hours. The mixture was cooled and some of the excess triethylamine removed by evaporation under reduced pressure.

The solid material was filtered under nitrogen, washed with acetonitrile (20 ml) and diethylether (50 ml) and then dried under reduced pressure to give a colourless solid (12.1 g, 45%).

$^1$H NMR (200 MHz) d (D$_2$O) 6.45 (1H,dd,J1.2 and 17.1 Hz), 6.25 (1H,dd,J1.2 and 10.25 Hz), 6.02 (1H,dd, J1.23 and 10.25 Hz), 4.4 (2H,m), 4.3 (2H, m), 4.2 (2H,m) 3.6(2H,m) and 3.2(9H,s) ppm.

Reference Example 5

Dodec-7-yn-1-yl Methacrylate

To dodec-7-yn-1-ol (25 g) in dichloromethane (60 ml) was added distilled triethylamine (14.1 g). The mixture was cooled in an ice bath (0.5° C.) and stirred as distilled methacryloyl chloride (16.2 g) in dichloromethane (50 ml) was added over 10 minutes. The temperature of the reaction was allowed to warm to ambient and the mixture stirred for two hours. Water (150 ml) was added and the organic layer was removed and successively extracted with water (2×150 ml) and saturated sodium bicarbonate solution (2×150 ml), washed with brine (150 ml) and dried over anhydrous sodium sulphate. The solvent was removed under reduced pressure to give a pale yellow oily liquid which was distilled under reduced pressure (0.18 mBar, 106–110° C.) in the presence of copper (1)chloride to give dodec-7-yn-1-yl methacrylate, 17 g, 50% yield.

$^1$H-NMR (200 MHz, d, ppm, CDCl$_3$): 0.90 (t,3H), 1.45 (m,10H), 1.70 (m,2H), 1.95 (s,3H), 2.15 (m,6H), 4.15 (t,2H), 5.55 (s,1H), 6.10 (s,1H).

Reference Example 6

Preparation of Poly(2(methacryloyloxyethyl)-2'-(trimethylammonium)ethyl Phosphate Inner Salt-co-n-dodecyl Methacrylate (1:2)

2(Methacryloyloxyethyl)-2'-(trimethylammonium)ethyl phosphate inner salt (12.06 g, 0.0409 mole) and n-dodecyl methacrylate (20.52 g, 0.0808 mole) were dissolved in propan-2-ol (215 ml) and ethyl acetate (85 ml). The solution was stirred (250 rpm) at 23° C. under a stream of nitrogen (50 ml/min) for 30 minutes, 2,2'-azo-bis(2-methylpropionitrile) (0.0645 g, 0.39 mmole) was added and the flow of nitrogen was reduced to 10 ml/min, the reaction temperature was raised to 60° C. This temperature and nitrogen flow rate were maintained for 40 hours.

The mixture was allowed to cool and vacuum filtered. The filtrate was evaporated to dryness using a rotary evaporator and dissolved in dichloromethane (120 ml) and methanol (10 ml). The polymer was isolated from this mixture by precipitation in acetone (2500 ml), vacuum filtration and drying. The polymer was redissolved in dichloromethane (100 ml) and methanol (30 ml) and isolated as described above.

The resulting polymer, obtained in 70–80% yield was a white powder.

NMR(200MHz, d, ppm, CD$_3$OD/CDCl$_3$) 4.2–4.4 (b), 3.8–4.2 (b), 3.6–3.8 (b), 3.3 (s), 1.8–2.2 (b), 1.5–1.8 (b), 1.2–1.5 (s), 0.8–1.0 (s); IR(cm$^{-1}$, KBr disc) 3430, 2929, 2854, 1732, 1469, 1246, 1156, 1089, 968, 788. Elemental Analysis; theory C, 64.5, H, 9.9, N, 1.8, P, 3.9; actual C, 59.0, H, 10.0, N, 1.8, P, 3.9.

The polymer had a relative viscosity in ethanol: chloroform (50:50) at 250° C. of 1.13±0.02 (when prepared using methanol: THF as solvent) and 1.26±0.02 (when prepared using propan-2-ol: ethylacetate as solvent).

Reference Example 7

Preparation of Poly(2(methacryloyloxyethyl)-2'-(trimethylammonium)ethyl Phosphate Inner Salt-co-n-octadecyl Methacrylate (1:2)

The polymer was obtained by an analogous procedure to that described in Reference Example 6 using 2(methacryloyloxyethyl)-2'-(trimethylammonium)ethyl phosphate inner salt (3.0 g, 0.0102 mole) and n-octadecyl methacrylate (6.9 g, 0.0204 mole) dissolved in methanol (30 ml) and THF (70 ml).

The resulting polymer, obtained in 55% yield was a white solid.

NMR(100MHz, d, ppm, CD$_3$OD/CDCl$_3$) 4.2–4.4 (b), 3.8–4.2 (b), 3.6–3.8 (b), 3.3 (s), 1.8–2.2 (b), 1.5–1.8 (b), 1.2–1.5 (s), 0.8–1.0 (s); IR(cm$^{-1}$, KBr disc) 3430, 2929, 2854, 1732, 1469, 1246, 1156, 1089, 968, 788.

The polymer had a relative viscosity in ethanol: chloroform (50.50) at 25° C. of 1.26±0.02.

Reference Example 8

Preparation of Poly(methacryloyloxyethyl-2'-(trimethylammonium)ethyl Phosphate Inner Salt-co-methacryloylethyltrimethylammonium Bromide (7:3)

(Methacryloyloxyethyl)-2'-(trimethylammonium)ethyl phosphate inner salt (4.5 g) and methacryloylethyltrimethylammonium bromide 75% aqueous solution (2.0 g) were dissolved in ethanol (50 ml) and the solution purged with nitrogen (30 minutes). 2,2'azo-bis(2-methylpropionitrile) (0.020 g) was added and the temperature raised to 60° C. The reaction solution was stirred under nitrogen for 24 hours then the solution allowed to cool to room temperature. The polymer was isolated by precipitation in acetone (500 ml) followed by vacuum filtration under a nitrogen atmosphere. The product was then dried under vacuum at room temperature to give a yield of 4.0 g (67%).

NMR (200MHz, d, ppm, CD$_3$OD)4.2–4.4(b), 4.1–4.3(b), 4.0–4.2(b), 3.7(b), 3.3(s), 1.8–2.2(b), 1.2–1.4 (b), 1.0–1.2 (b),0.8–1.1(b) IR(cm$^{-1}$, KBr disc) 3426, 2959, 1724, 1484, 1245, 1166, 1078, 969, 791

Reference Example 9

Preparation of Poly(methacryloyloxyethyl)-2'-(trimethylammonium)ethyl Phosphate Inner Salt-co-3-chloro-2-hydroxypropylmethacrylate (4:1)

(Methacryloyloxyethyl)-2'-(trimethylammonium)ethyl phosphate inner salt (8.50 g) and 3-chloro-2-hydroxypropylmethacrylate (1.26 g) were dissolved in propan-2-ol (97.6 g) and the solution purged with nitrogen (30 minutes). 2,2'azo-bis(2-methylpropionitrile) (0.012 g) was added and the temperature raised to 60° C. The reaction solution was stirred under nitrogen for 16 hours then ethanol was added. The solution was then allowed to cool to room temperature and the polymer isolated by precipitation in acetone (1.5 L) followed by vacuum filtration under a nitrogen atmosphere. The crude product was dried under vacuum at room temperature then redissolved in ethanol (100 ml). The final product was isolated by precipitation in ethyl acetate/acetone (80:20) solution (1.5L) followed by vacuum filtration under a nitrogen atmosphere. The solid was dried under vacuum at room temperature to give a yield of 8.3 g (85%).

NMR (200 MHz, d, ppm, CD$_3$OD)4.4–4.6(b), 4.2–4.4(b), 4.1–4.3(b), 4.0–4.2(b), 3.7–3.9(b), 3.6–3.8(b) 3.3(s), 1.8–2.2 (b), 1.1–1.4(b), 1.0–1.2(b), 0.9–1.1(b); IR(cm$^{-1}$, KBr disc) 3446, 2960, 1724, 148.4, 1245, 1164, 1089, 970, 790.

Reference Example 10

Preparation of Poly(methacryloyloxyethyl)-2'-(trimethylammonium)ethyl Phosphate Inner Salt-co-n-butylmethacrylate (1:2)

(Methacryloyloxyethyl)-2'-(trimethylammonium)ethyl phosphate inner salt (21.93 g) and n-butylmethacrylate (21.14 g) were dissolved in ethyl acetate/propan-2-ol (28:72) solution (545 ml) and the solution purged with nitrogen (30 minutes). 2,2'-azo-bis(2-methylpropionitrile) (0.119 g) was added and the temperature raised to 62° C. the reaction solution was stirred under nitrogen for 40 hours then the solution allowed to cool to 40° C. The solvent was removed on a rotary evaporator and the solid redissolved in dichloromethane/methanol (92:8) solution (153 ml). The polymer was isolated by precipitation in diethylether (1.75 L) followed by vacuum filtration under a nitrogen atmosphere. The crude product was dried under vacuum at room temperature then redissolved in dichloromethane/methanol (92.:8) solution (153 ml). The final product was isolated by precipitation in diethylether (1.75 L) followed by vacuum filtration under a nitrogen atmosphere. The solid was dried under vacuum at room temperature to give a yield of 31.2 g (72%).

NMR (200 MHz, d, ppm, CD$_3$OD)4.2–4.4(b), 4.0–4.2(b), 3.9–4.1(b), 3.6–3.8(b), 3.3(s), 1.7–2.0(b), 1.6–1.8(b), 1.4–1.6(b), 0.8–1.2(s); IR(cm$^{-1}$, KBr disc) 3436, 2961, 1728, 1489, 1244, 1165, 1088, 959, 793; Elemental Analysis; theory C, 55.97; H, 8.71; N, 2.42; actual C, 51.95; H, 8.41; N, 2.65.

Reference Example 11

Preparation of Poly(methacryloyloxyethyl)-2'-(trimethylammonium)ethyl Phosphate Inner Salt-co-dodecylmethacrylate-co-1H,1H, 2H,2H-heptadecafluorodecylmethacrylate (1:1:1)

(Methacryloyloxyethyl)-2'-(trimethylammonium)ethyl phosphate inner salt (7.23 g), dodecylmethacrylate (2.35 g) and 1H,1H,2H,2H-heptadecafluorodecylmethacrylate (4.92 g) were dissolved in ethyl acetate/propan-2-ol (50:50) solution (100 ml) and the solution purged with nitrogen (30 minutes). 2,2'azo-bis(2-methylpropionitrile) (0.016 g) was added and the temperature raised to 60° C. The reaction solution was stirred under nitrogen for 40 hours then the solution allowed to cool to room temperature. The solvent was removed on a rotary evaporator and the solid redissolved in dichloromethane (30 ml). The polymer was isolated by precipitation in acetone (1.5 L) followed by vacuum filtration under a nitrogen atmosphere. The product was then dried under vacuum at room temperature to give a yield of 8.3 g (83%).

Reference Example 12

Preparation of Natural Rubber Latex Sheet

Natural rubber latex (6.00 g, 37% soids) was added to water (6.00 g) with stirring. The mixture was then cast on to a glass plate in a well formed by a sheet of PTFE with the centre removed clamped to the glass with bulldog clips. The cast film was then cured in an oven at 140° C. for 20 minutes. The pale brown transparent sheet was then allowed to cool to room temperature then washed repeatedly with water (wetting poorly) to give a cream coloured opaque sheet. The sheet had a high degree of self tackiness and readily stuck to itself irreversibly.

Reaction Scheme A

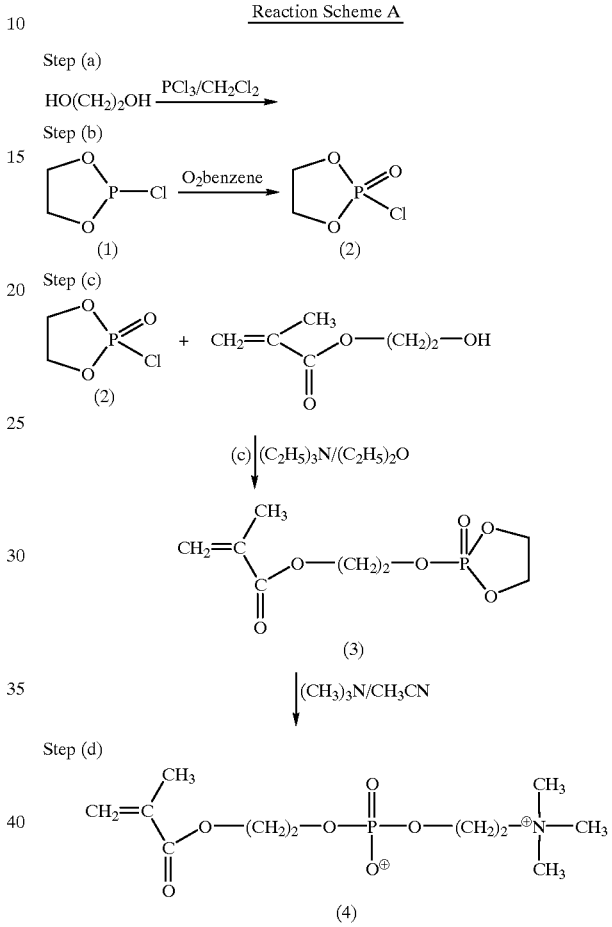

Steps (a) to (d) correspond with the steps in Reference

Reaction Scheme B

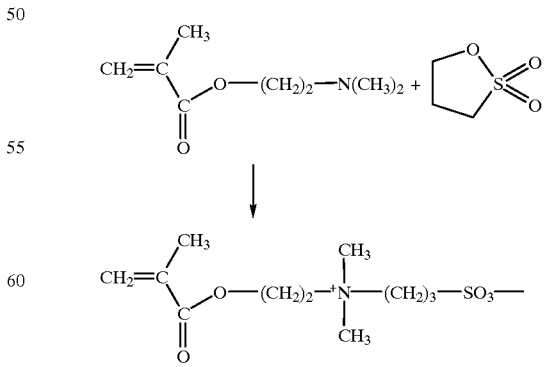

Reaction Scheme C

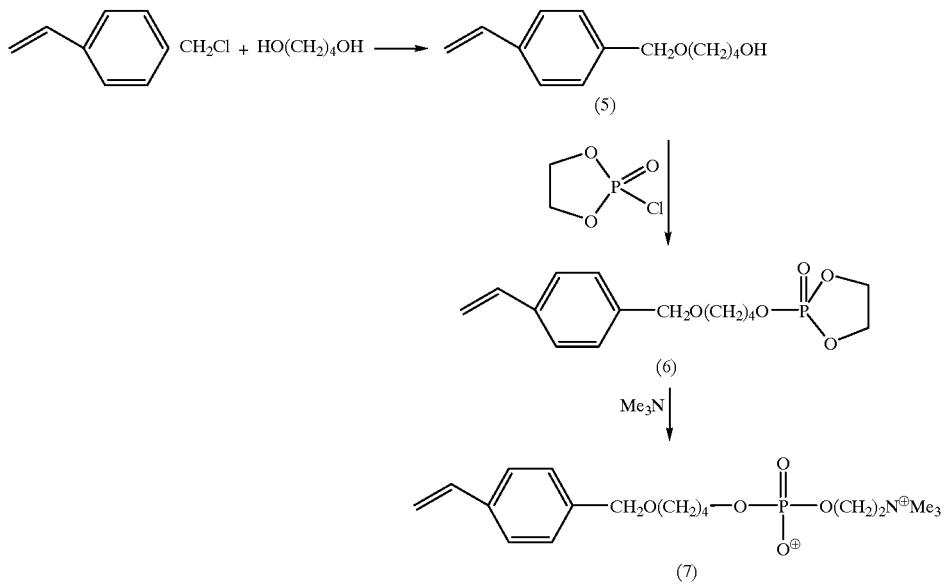

What is claimed is:

1. A liquid composition consisting essentially of a liquid vehicle and, dissolved or dispersed in the liquid vehicle, a zwitterionic polymer having pendant zwitterionic groups X, in which X is IVB

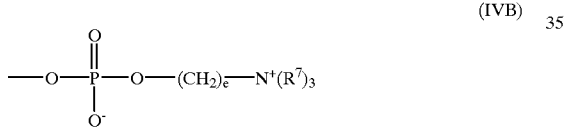

(IVB)

where the $R^7$ groups are the same or different and each is hydrogen or a $C_{1-4}$ alkyl group, and e is from 1 to 4;
a polymer having desirable physical and/or mechanical characteristics which is a thermoplastic or an elastomeric polymer; and
at least one additive selected from the group consisting of plasticisers, fillers, colourants, UV absorbers, antioxidants and preservatives.

2. A composition according to claim 1 in which the polymer having desirable mechanical and/or physical properties is less hydrophilic than the zwitterionic polymer.

3. A composition according to claim 1 in which the polymer have desirable mechanical and/or physical properties is selected from the group consisting of polyolefins, vinyl halide polymers, (alk)acrylate polymers, polyurethanes, natural rubbers and synthetic rubbers.

4. A composition according to claim 1 in which the zwitterionic polymer is formed from radical polymerisable monomers including a zwitterionic monomer of formula (I)

(I)

wherein B is a straight or branched alkylene, an oxaalkylene or an oligo-oxaalkylene chain optionally containing one or more fluorine atoms up to and including perfluorinated chains, or if X contains a carbon-carbon chain between B and the zwitterionic moiety or if Y contains a terminal carbon bonded to B, a valence bond;

X is said zwitterionic group,
Y is an ethylenically unsaturated polymerisable group selected from the group consisting of

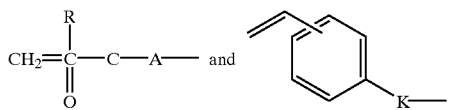

wherein:
R is hydrogen or a $C_1$–$C_4$ alkyl group;
A is —O— or $NR^1$— where $R^1$ is hydrogen or a $C_1$–$C_4$ alkyl group or is —B—X where B and X are as defined above; and
K is: —$(CH_2)_pOC(O)$—, —$(CH_2)_pC(O)O$—, —$(CH_2)_pOC(O)O$—, —$O(CH_2)_pNR^2$—, —$(CH_2)_pNR^2C(O)$—, —$(CH_2)_pC(O)NR^2$—, —$(CH_2))NR^2C(O)O$—, —$(CH_2)_pOC(O)NR^2$—, —$(CH_2)_pNR^2C(O)NR^2C(O)NR^2$— (in which the $R^2$ groups are the same or different) —$(CH_2)_pO$—, —$(CH_2)_pSO_3$—, or, optionally in combination with B, a valence bond and p is from 1 to 12 and $R^2$ is hydrogen or a $C_1$–$C_4$ alkyl group.

5. A composition according to claim 4 wherein X is a zwitterionic group in which the anionic moiety is a phosphate group.

6. A composition according to claim 4 in which the zwitterionic monomer is of the formula

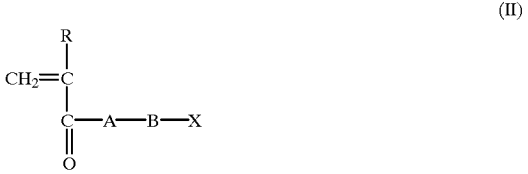

(II)

in which R is hydrogen, methyl, or ethyl, and A, B and X are defined in claim 4.

7. A composition according to claim 6 in which R is methyl.

8. A composition according to claim 1 in which the $R^7$ groups are all methyl.

9. A composition according to claim 4 in which the zwitterionic polymer is formed from monomers including a comonomer of the formula (IX)

   (IX)

where $Y^1$ is an ethylenically unsaturated polymerisable group selected from the group consisting of

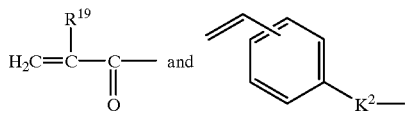

where $R^{19}$ is hydrogen or a $C_1$–$C_4$ alkyl group $K^2$ is: —$(CH_2)_qOC(O)$—, $(CH_2)_qC(O)O$—, —$(CH_2)_qOC(O)O$—, —$(CH_2)_qNR^{20}$—, —$(CH_2)_qNR^{20}C(O)$—, —$(CH_2)_qC(O)NR^{20}$—, —$(CH_2)_qNR^{20}C(O)O$—, —$(CH_2)_qOC(O)NR^{20}$—, —$(CH_2)_qNR^{20}C(O)NR^{20}$— (in which the groups $R^{20}$ are the same or different), —$(CH_2)_qO$—, —$(CH_2)_qSO_3$—, or a valence bond and q is from 1 to 12 and $R^{20}$ is hydrogen or a $C_1$–$C_4$ alkyl group; and $Q^1$ is a reactive group capable of reacting to provide crosslinking within the polymer having desirable physical and/or mechanical properties or to the zwitterionic polymer and/or providing a reactive group on the surface of the blend.

10. A composition according to claim 9 in which the comonomer is a compound of formula X

   (X)

wherein:

$Q^2$ is hydrogen, —OH or a group of the formula:

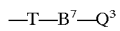

where T is —O—, or —$NR^{21}$—, where $R^{21}$ is hydrogen, $C_1C_4$ alkyl or a group —$B^7$—$Q^3$;

wherein $B^7$ is a valence bond or a straight or branched alkylene, an oxaalkylene or an oligo-oxaalkylene chain; and $Q^3$ is a reactive group selected from the group consisting of:
i) an aldehyde group,
ii) silane and siloxane groups containing one or more reactive substituents selected from the group consisting of a halogen or an alkoxy containing from 1 to 4 carbon atoms,
iii) a hydroxyl group,
iv) an amino group,
v) a carboxyl group,
vi) an epoxy group,
vii) —$CHOHCH_2Hal$, in which Hal is a halogen atom,
viii) a succinimido group,
ix) sulphonic acid ester groups,
x) an imidazole carbonyl-amino group and
xi) optionally substituted triazine groups.

11. A composition according to claim 10 in which $B^7$ is selected from the group consisting of —$CH_2$—, —$CH_2CH_2$— and —$(CH_2)_6$—.

12. A composition according to claim 4 in which the zwitterionic polymer is formed from monomers including a compound of the formula XII

   (XII)

where $Y^2$ is an ethylenically unsaturated polymerisable group selected from the group consisting of

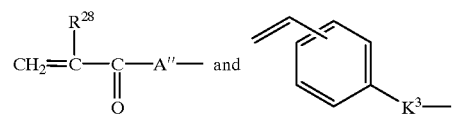

where $R^{28}$ is hydrogen or a $C_1$–$C_4$ alkyl group;

A" is —O— or —$NR^{27}$—, wherein $R^{27}$ is hydrogen a $C_1$–$C_4$ alkyl group or a —$B^9$—$Q^5$ group;

$B^9$ is a valence bond, a straight or branched alkylene, an oxaalkylene or an oligo-oxaalkylene group;

$K^3$ is: —$(CH_2)_xOC(O)$—, —$(CH_2)_xC(O)O$—, —$(CH_2)_xOC(O)O$—, —$(CH_2)_xNR^{28}$—, —$(CH_2)_xNR^{28}C(O)$—, —$(CH_2)_xCONR^{28}$—, —$(CH_2)_xNR^{20}C(O)O$—, —$(CH_2)_xOC(O)NR^{28}$—, —$(CH_2)_xNR^{28}C(O)NR^{28}$— (in which the groups $R^{28}$ are the same or different), —$(CH_2)_xO$—, —$(CH_2)_xSO_3$—, or a valence bond (optionally in combination with $B^9$) and x is from 1 to 12 and $R^{28}$ is hydrogen or a $C_1$–$C_4$ alkyl group; and $Q^5$ is an ionic group.

13. A composition according to claim 4 in which the zwitterionic polymer is formed from monomers including a compound selected from the group consisting of acrylic acid, methacrylic acid, 2-sulphoethyl methacrylate, 2-methacryloyloxyethyl phosphate, p-styrene sulphonic acid, 2-(methacryloyloxyethyl)trimethyl ammonium chloride, 3-aminopropyl methacrylamide and vinyl benzyl trimethyl anmionium chloride.

14. A composition according to claim 4 in which the zwitterionic polymer is formed from monomers including a diluent comonomer selected from the group consisting of alkyl (alk)acrylates containing 1 to 4 carbon atoms in the alkyl group, mono- and di-alkyl amino alkyl (alk)acrylates containing 1 to 4 carbon atoms in each alkyl moiety; (alk)acrylamides; mono- or di-alkyl (alk)acrylamides containing 1 to 4 carbon atoms in the alkyl groups; hydroxy alkyl (alk)acrylates containing 1 to 4 carbon atoms in the hydroxyalkyl group; N-vinyl lactam containing from 4 to 7 atoms in the lactam ring; vinyl acetate; styrene; a styrene compound substituted by one or more alkyl groups containing 1 to 6 carbon atoms and/or by one or more halogen atoms; polyhydroxyl (alk)acrylates and polyhydroxyl (alk)acrylamides; $C_{2-4}$-alkenes; butadiene; maleic anhydride and acrylonitrile.

15. A composition according to claim 4 in which the amount of the zwitterionic polymer in the liquid blend is in the range of 1 to 90% by weight, based on the total weight of zwitterionic polymer and polymer having desirable mechanical and/or physical properties.

16. A composition according to claim 4 in which the liquid vehicle is selected from the group consisting of water, methanol, dichloromethane, pyrrolidinone, ethylacetate and isopropanol.

17. A composition comprising a liquid vehicle and, dissolved or dispersed in the liquid vehicle a zwitterionic polymer having pendant zwitterionic groups, a polymer having desirable physical and/or mechanical characteristics which is a thermoplastic or an elastomeric polymer, in which the zwitterionic polymer is formed from a radical polymerisable zwitterionic monomer of formula (I)

Y—B—X (I)

wherein B is a straight or branched alkylene, an oxaalkylene or an oligo-oxaalkylene chain optionally containing one or more fluorine atoms up to and including perfluorinated chains, or if X contains a carbon-carbon chain between B and the zwitterionic moiety or if Y contains a terminal carbon bonded to B, a valence bond;

X is a group of formula IVB

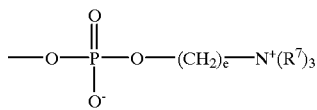
(IVB)

where the $R^7$ groups are the same or different and each is hydrogen or a $C_{1-4}$ alkyl group, and e is from 1 to 4;

Y is an ethylenically unsaturated polymerisable group selected from the group consisting of

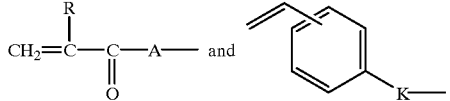

wherein:

R is hydrogen or a $C_1$–$C_4$ alkyl group;

A is —O— or $NR^1$— where $R^1$ is hydrogen or a $C_1$–$C_4$ alkyl group or $R^1$ is —B—X where B and X are as defined above; and K is: —$(CH_2)_pOC(O)$—, —$(CH_2)_pC(O)O$—, —$(CH_2)_pOC(O)O$—, —$O(CH_2)_pNR^2$—, —$(CH_2)_pNR^2C(O)$—, —$(CH_2)_pC(O)NR^2$—, —$(CH_2)NR^2C(O)O$—, —$(CH_2)_pOC(O)NR^2$—, —$(CH_2)_pNR^2C(O)NR^2$— (in which $R^2$ groups are the same or different), —$(CH_2)_pSO_3$—, or, optionally in combination with B, a valence bond and p is from 1 to 12 and $R^2$ is hydrogen or a $C_1$–$C_4$ alkyl group.

18. A composition according to claim 17 in which Y is $CH_2=C(R)C(O)$— in which R is selected from the group consisting of hydrogen, methyl and ethyl.

19. A composition according to claim 17 in which the groups $R^7$ are all methyl.

20. A composition according to claim 17 in which the zwitterionic polymer is formed from monomers including a comonomer of the formula (IX)

$Y^1Q^1$ (IX)

where $Y^1$ is an ethylenically unsaturated polymerisable group selected from the group consisting of

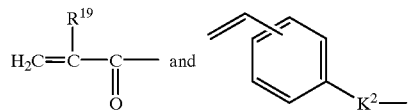

where $R^{19}$ is hydrogen or a $C_1$–$C_4$ alkyl group $K^2$ is: —$(CH_2)_qOC(O)$—, $(CH)_qC(O)O$—, $(CH_2)_qOC(O)O$—, —$(CH_2)_qNR^{20}$—, —$(CH_2)_qNR^{20}C(O)$—, —$(CH_2)_qC(O)NR^{20}$—, —$(CH_2)_qNR^{20}C(O)O$—, —$(CH_2)_qOC(O)NR^{20}$, —$(CH_2)_qNR^{20}C(O)NR^{20}$— (in which the groups $R^{20}$ are the same or different), —$(CH_2)_qO$—, or —$(CH_2)_qSO_3$—, or a valence bond and q is from 1 to 12 and $R^{20}$ is hydrogen or a $C_1$–$C_4$ alkyl group; and $Q^1$ is a reactive group capable of reacting to provide crosslinking within the polymer having desirable physical and/or mechanical properties or to the zwitterionic polymer and/or providing a reactive group on the surface of the blend.

21. A composition according to claim 17 in which the comonomer is a compound of formula X

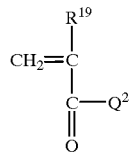
(X)

wherein:

$Q^2$ is hydrogen, —OH or a group of the formula:

—T—$B^7$—$Q^3$ where T is —O—, or —$NR^{21-}$ where $R^{21}$ is hydrogen, $C_{1-4}$ alkyl or a group —$B^7$—$Q^3$;

wherein $B^7$ is a valence bond or a straight or branched alkylene, an oxaalkylene or an oligo-oxaalkylene chain; and $Q^3$ is a reactive group selected from the group consisting of:
i) an aldehyde group,
ii) silane and siloxane groups containing one or more reactive substituents selected from the group consisting of a halogen or an alkoxy containing from 1 to 4 carbon atoms,
iii) a hydroxyl group,
iv) an amino group,
v) a carboxyl group,
vi) an epoxy group,
vii) —$CHOHCH_2Hal$, in which Hal is a halogen atom,
viii) a succinimido group,
ix) sulphonic acid ester groups,
x) an imidazole carbonyl-amino group and
xi) optionally substituted triazine groups.

22. A composition according to claim 21 in which $B^7$ is selected from the group consisting of —$CH_2$—, —$CH_2CH_2$— and —$(CH_2)_6$—.

23. A composition according to claim 17 in which the zwitterionic polymer is formed from monomers including a compound of the formula XII $Y^2$—$B^9$—$Q^5$ (XII)

where $Y^2$ is an ethylenically unsaturated polymerisable group selected from the group consisting of

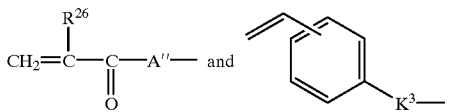

where $R^{26}$ is hydrogen or a $C_1$–$C_4$ alkyl group;

A″ is —Q— or —NR$^{27}$—, wherein $R^{27}$ is hydrogen a $C_1$–$C_4$ alkyl group or a —B$^9$—Q$^5$ group;

B$^9$ is a valence bond, a straight or branched alkylene, an oxaalkylene or an oligo-oxaalkylene group;

$K^3$ is: —(CH$_2$)$_x$OC(O)—, —(CH$_2$)$_x$C(O)O—, —(CH$_2$)$_x$OC(O)O—, —(CH$_2$)$_x$NR$^{28}$—, —(CH$_2$)$_x$NR$^{28}$C(O)—, —(CH$_2$)$_x$CONR$^{28}$—, —(CH$_2$)$_x$NR$^{20}$C(O)O—, —(CH$_2$)$_x$OC(O)NR$^{28}$—, —(CH$_2$)$_x$NR$^{28}$C(O)NR$^{28}$— (in which the groups $R^{28}$ are the same or different), —(CH$_2$)$_x$O—, —(CH$_2$)$_x$SO$_3$—, or a valence bond (optionally in combination with B$^9$) and x is from 1 to 12 and $R^{28}$ is hydrogen or a $C_1$–$C_4$ alkyl group; and $Q^5$ is an ionic group.

24. A composition according to claim 17 in which the zwitterionic polymer is formed from monomers including a compound selected from the group consisting of acrylic acid, methacrylic acid, 2-sulphoethyl methacrylate, 2-methacryloyloxyethyl phosphate, p-styrene sulphonic acid, 2-(methacryloyloxyethyl)trimethyl ammonium chloride, 3-aminopropyl methacrylamide and vinyl benzyl trimethyl ammonium chloride.

25. A composition according to claim 17 in which the zwitterionic polymer is formed from monomers including a diluent comonomer selected from the group consisting of alkyl (alk)acrylates containing 1 to 4 carbon atoms in the alkyl group, mono- and di-alkyl amino alkyl (alk)acrylates containing 1 to 4 carbon atoms in each alkyl moiety; (alk)acrylamides; mono- or di-alkyl (alk)acrylamides containing 1 to 4 carbon atoms in the alkyl groups; hydroxy alkyl (alk)acrylates containing 1 to 4 carbon atoms in the hydroxyalkyl group; N-vinyl lactam containing from 4 to 7 atoms in the lactam ring; vinyl acetate; styrene; a styrene compound substituted by one or more alkyl groups containing 1 to 6 carbon atoms and/or by one or more halogen atoms; polyhydroxyl (alk)acrylates and polyhydroxyl (alk)acrylamides; $C_{2-4}$-alkenes; butadiene; maleic anhydride and acrylonitrile.

26. A composition according to claim 17 in which the amount of the zwitterionic polymer in the liquid blend is in the range of 1 to 90% by weight, based on the total weight of zwitterionic polymer and polymer having desirable mechanical and/or physical properties.

27. A composition according to claim 17 in which the liquid vehicle is selected from the group consisting of water, methanol, dichloromethane, pyrrolidinone, ethylacetate and isopropanol.

28. A method of using a polymer bearing zwitterionic pendant groups to increase lubricity in the presence of an aqueous liquid of a polymer having desirable physical and/or mechanical properties, comprising the steps of:

blended a preformed polymer (A) bearing zwitterionic pendant groups with a polymer (B) having desirable physical and/or mechanical properties, and shaping the blend to form an article comprising the polymer bearing said zwitterionic pendant groups, wherein the zwitterionic pendant groups have a quaternary anmionium group as a cationic moiety.

29. A method of improving the biocompatibility of a polymer, comprising the steps of:

(1) providing a polymer having desirable mechanical and/or physical properties in a solution or dispersion in a liquid vehicle to provide a liquid polymer composition;

(2) dispersing or dissolving into the liquid polymer composition a zwitterionic polymer bearing zwitterionic pendant groups to produce a liquid blended composition, in which the zwitterionic polymer is included in an amount sufficient to reduce fibrinogen adsorption and/or platelet activation performance of the polymer having desirable physical and/or mechanical characteristics to less than 80% of the fibrinogen adsorption and/or platelet activation performance respectively of that polymer alone;

and (3) optionally in addition dispersing or dissolving into the liquid polymer composition or into the liquid blended composition at least one additive selected from the group consisting of plasticisers, fillers, colourants, UV absorbers, antioxidants and preservatives, said additives being biocompatible, and (4) removing the liquid vehicle from the liquid blended composition of step (2) or step (3) to provide a solid blend comprising the polymer bearing said zwitterionic pendant groups, wherein the zwitterionic pendant groups have a quaternary ammonium group as a cationic moiety.

* * * * *